(12) United States Patent
Powers et al.

(10) Patent No.: US 7,135,011 B2
(45) Date of Patent: Nov. 14, 2006

(54) PORTABLE DEVICE FOR DISPENSING SKIN TREATMENTS

(76) Inventors: Jeffrey Lewis Powers, 50114 E. Fellows Creek Ct., Plymouth, MI (US) 48170; Dennis Willard Davis, 427 E. Washington Ave., Eustis, FL (US) 32726; David Paul Thimm, 48770 Quail Run Dr. SW., Plymouth, MI (US) 48170; James Marvin Stenz, 7090 Linden Rd., Fenton, MI (US) 48430

( * ) Notice: Subject to any disclaimer, the term of this patent is extended or adjusted under 35 U.S.C. 154(b) by 0 days.

(21) Appl. No.: 10/729,757

(22) Filed: Dec. 5, 2003

(65) Prior Publication Data

US 2004/0162534 A1 Aug. 19, 2004

Related U.S. Application Data

(63) Continuation-in-part of application No. 10/314,825, filed on Dec. 9, 2002, now abandoned.

(60) Provisional application No. 60/515,718, filed on Oct. 30, 2003, provisional application No. 60/515,775, filed on Oct. 30, 2003, provisional application No. 60/515,793, filed on Oct. 30, 2003, provisional application No. 60/515,794, filed on Oct. 30, 2003.

(51) Int. Cl.
    *A61M 35/00* (2006.01)
(52) U.S. Cl. .................... 604/310; 604/311
(58) Field of Classification Search ............ 222/175, 222/212, 78, 79; 604/289, 309, 310, 311
    See application file for complete search history.

(56) References Cited

U.S. PATENT DOCUMENTS

| | | | |
|---|---|---|---|
| 4,058,237 A * | 11/1977 | Luke | 222/78 |
| 4,087,675 A | 5/1978 | Sansonetti | |
| 4,603,794 A | 8/1986 | DeFord et al. | |
| 4,689,935 A | 9/1987 | Harding | |
| 4,736,876 A | 4/1988 | Kriss | |
| 4,768,688 A * | 9/1988 | Harrigan | 224/148.2 |
| 5,088,624 A | 2/1992 | Hackett et al. | |
| 5,148,949 A | 9/1992 | Luca | |
| 5,289,948 A | 3/1994 | Moss et al. | |
| RE35,187 E * | 3/1996 | Gortz | 222/105 |
| 5,538,164 A | 7/1996 | Rivas | |
| 5,669,529 A | 9/1997 | Levit | |
| 5,678,730 A | 10/1997 | Fabek et al. | |
| 5,683,012 A | 11/1997 | Villaveces | |
| 5,815,467 A * | 9/1998 | Deering | 368/10 |
| 5,867,829 A | 2/1999 | Hegoas et al. | |
| D408,988 S | 5/1999 | Barber et al. | |
| 5,924,601 A | 7/1999 | Chen | |
| 5,927,548 A * | 7/1999 | Villaveces | 222/82 |
| 5,961,003 A | 10/1999 | Coryell | |
| 6,126,041 A | 10/2000 | DiTomasso | |
| 6,135,321 A | 10/2000 | Hippensteel | |
| 6,251,096 B1 | 6/2001 | Ostrow | |
| 6,283,334 B1 | 9/2001 | Mahaffey et al. | |
| 6,371,946 B1 | 4/2002 | Ostrow | |
| 6,540,107 B1 | 4/2003 | Admony | |
| 2002/0170927 A1 | 11/2002 | Gerstner | |

* cited by examiner

*Primary Examiner*—Tatyana Zalukaeva
*Assistant Examiner*—Ginger Chapman

(57) ABSTRACT

A portable, extremity-attachable device for dispensing skin treatment comprises a deformable housing having a skin treatment reservoir that is caused to dispense such treatment upon squeeze actuation. A set of valves permit proper operation of the device with different modes of use. Embodiments include a simple deformable, wrist-mounted device and a pumped based device with a rigid housing.

11 Claims, 34 Drawing Sheets

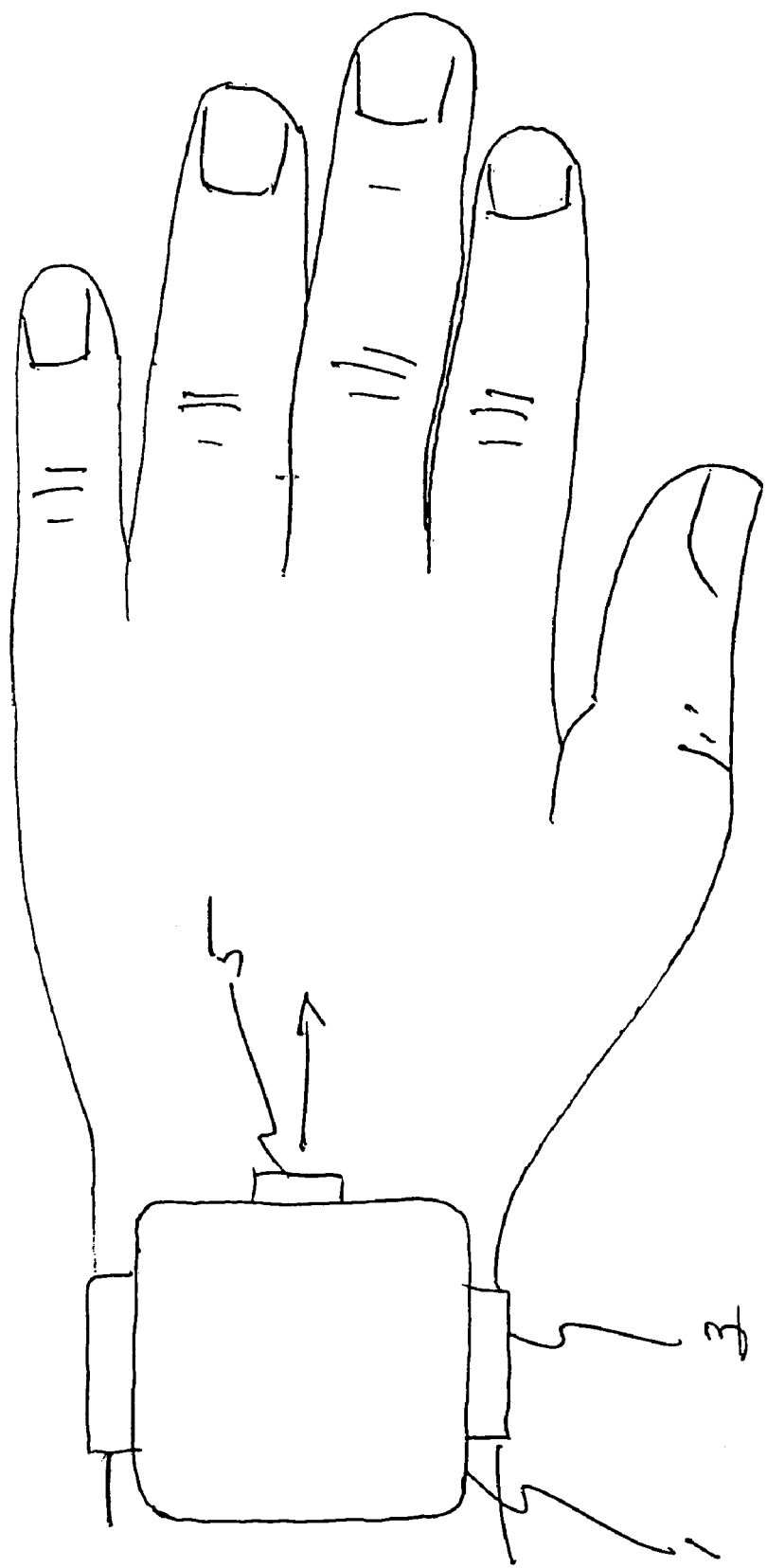

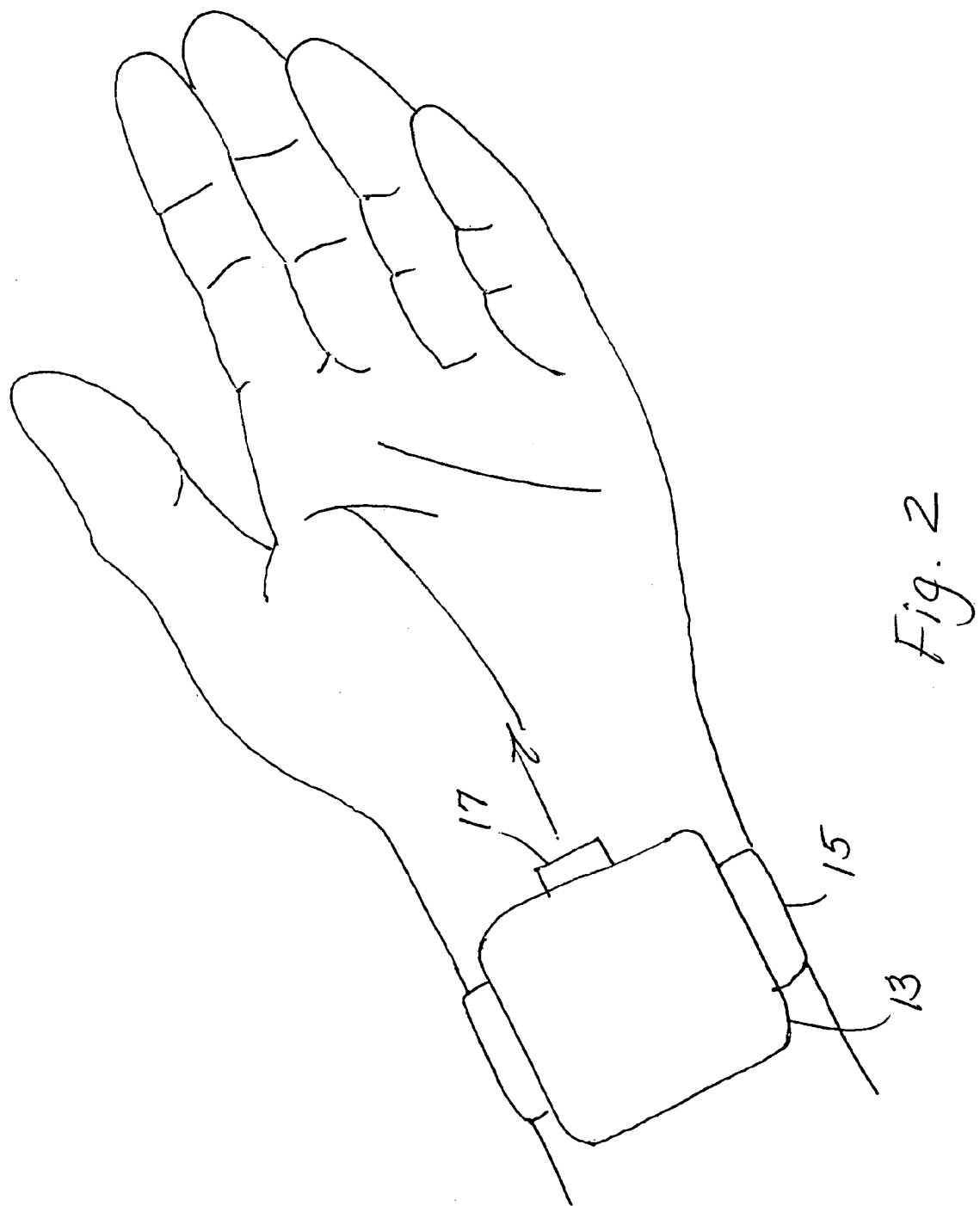

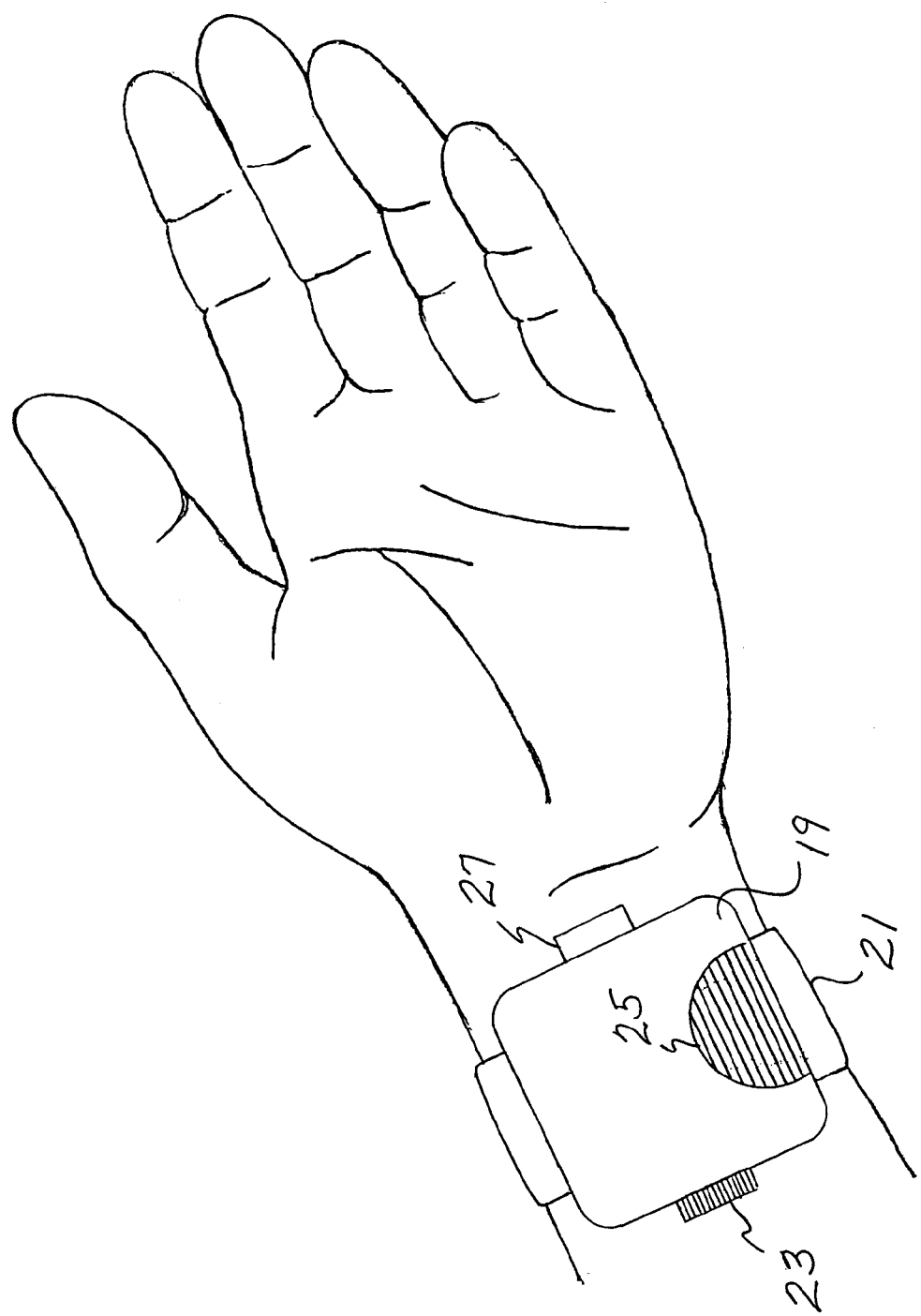

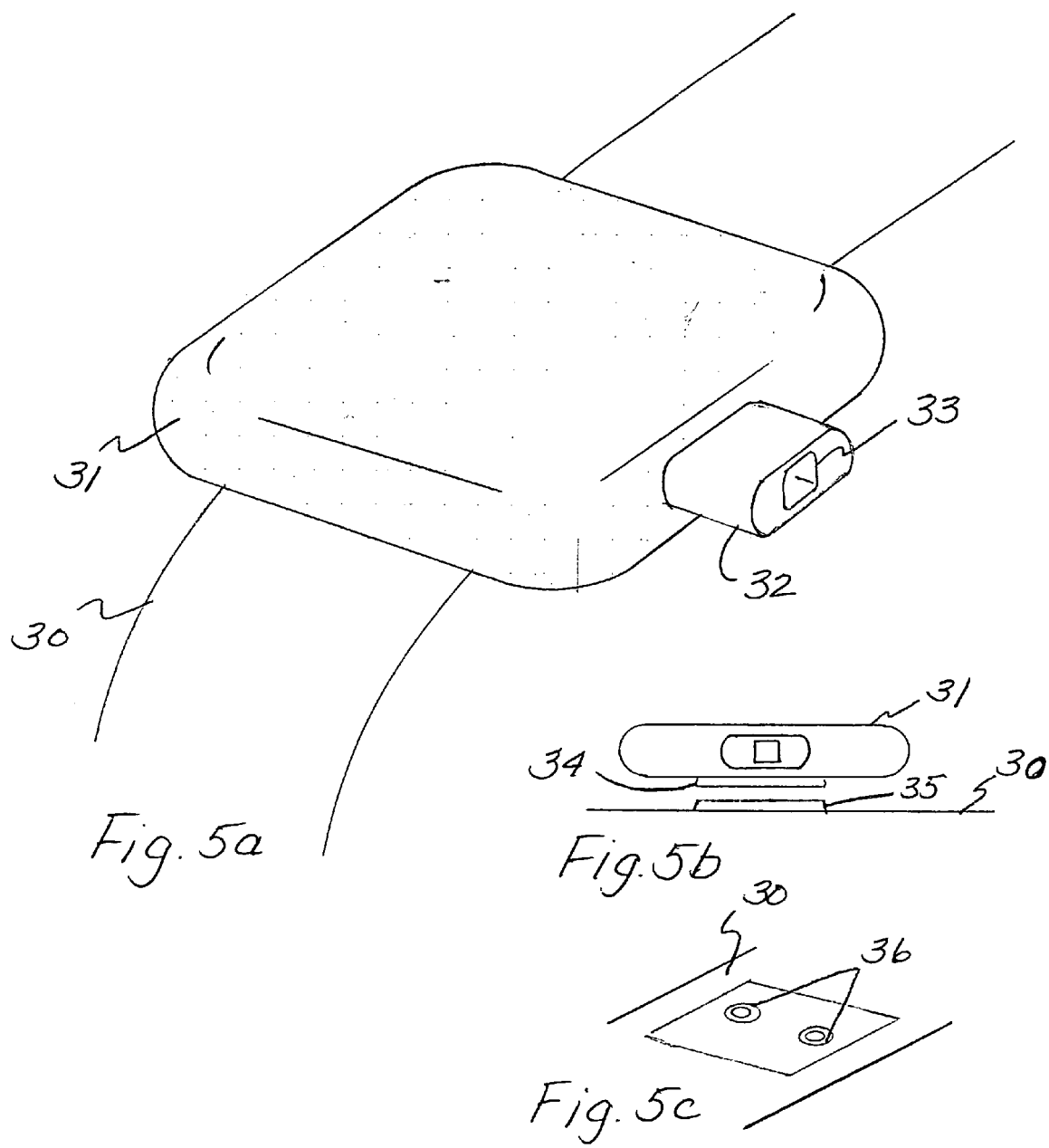

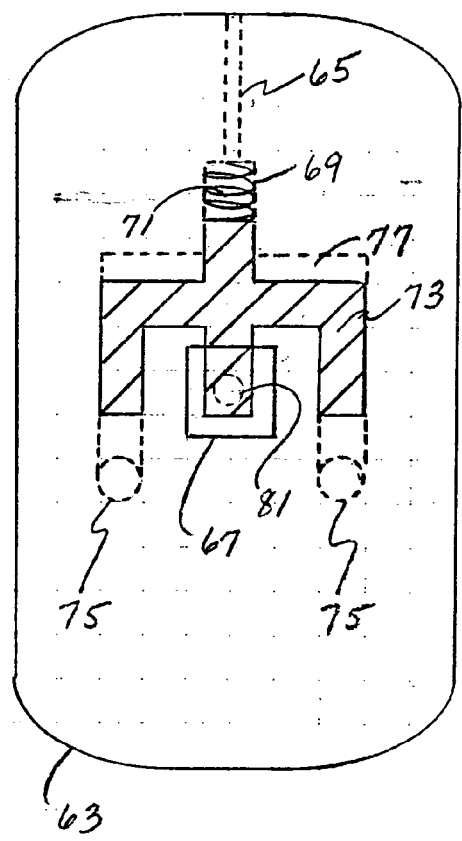
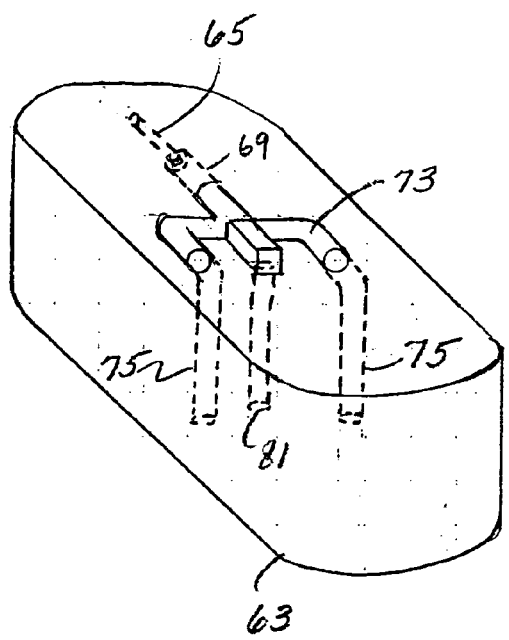
Fig. 6c
Fig. 6d

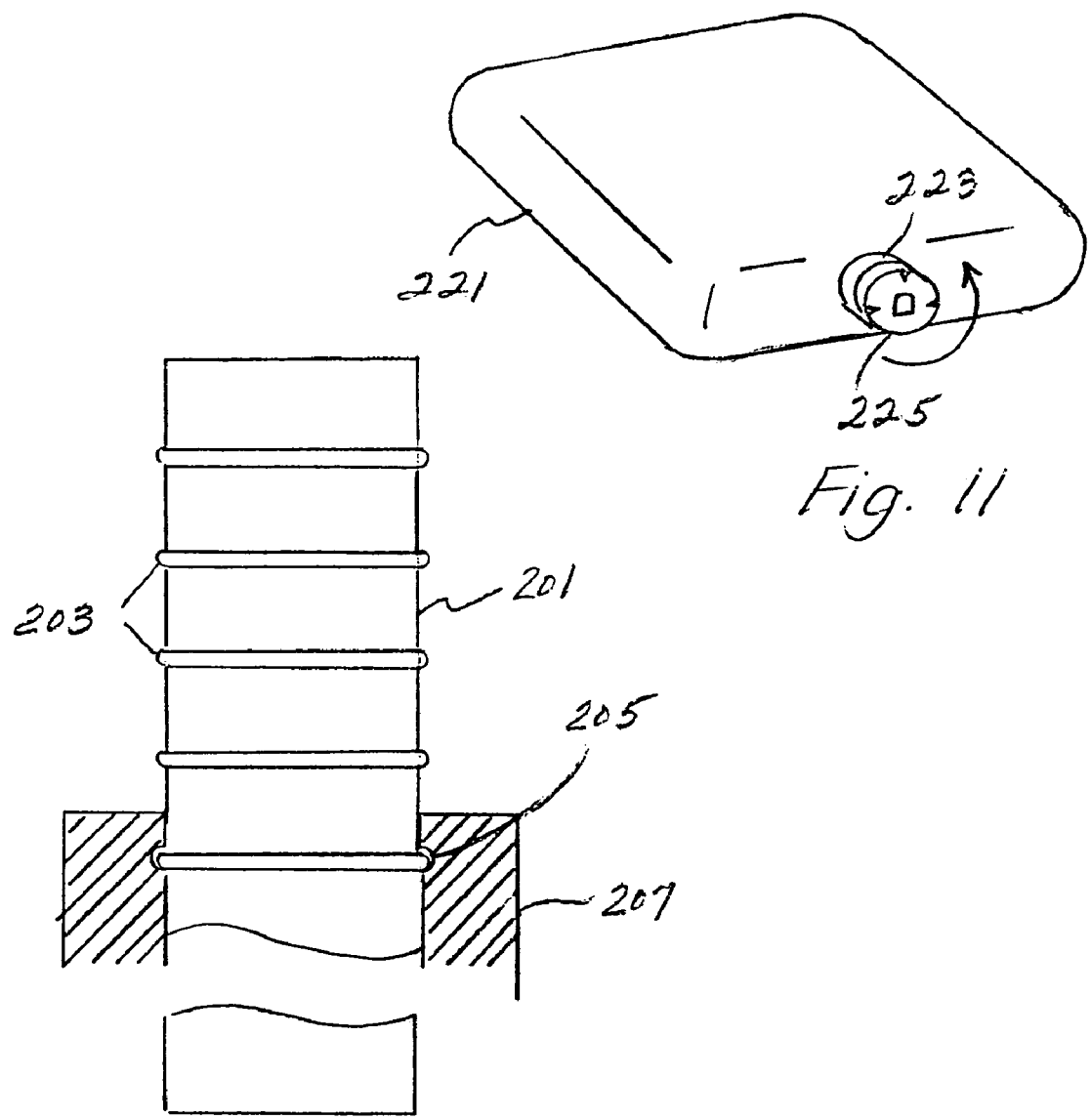

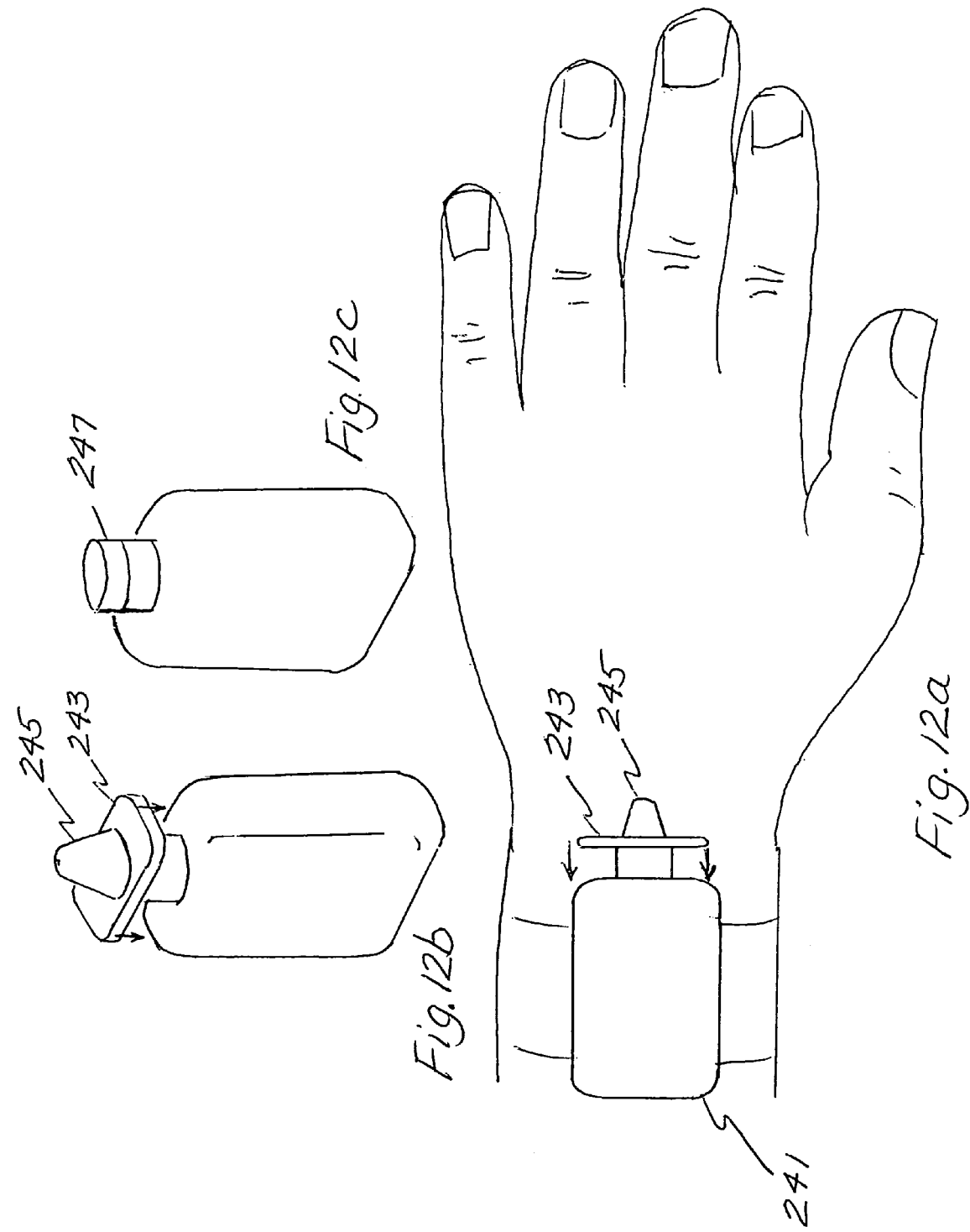

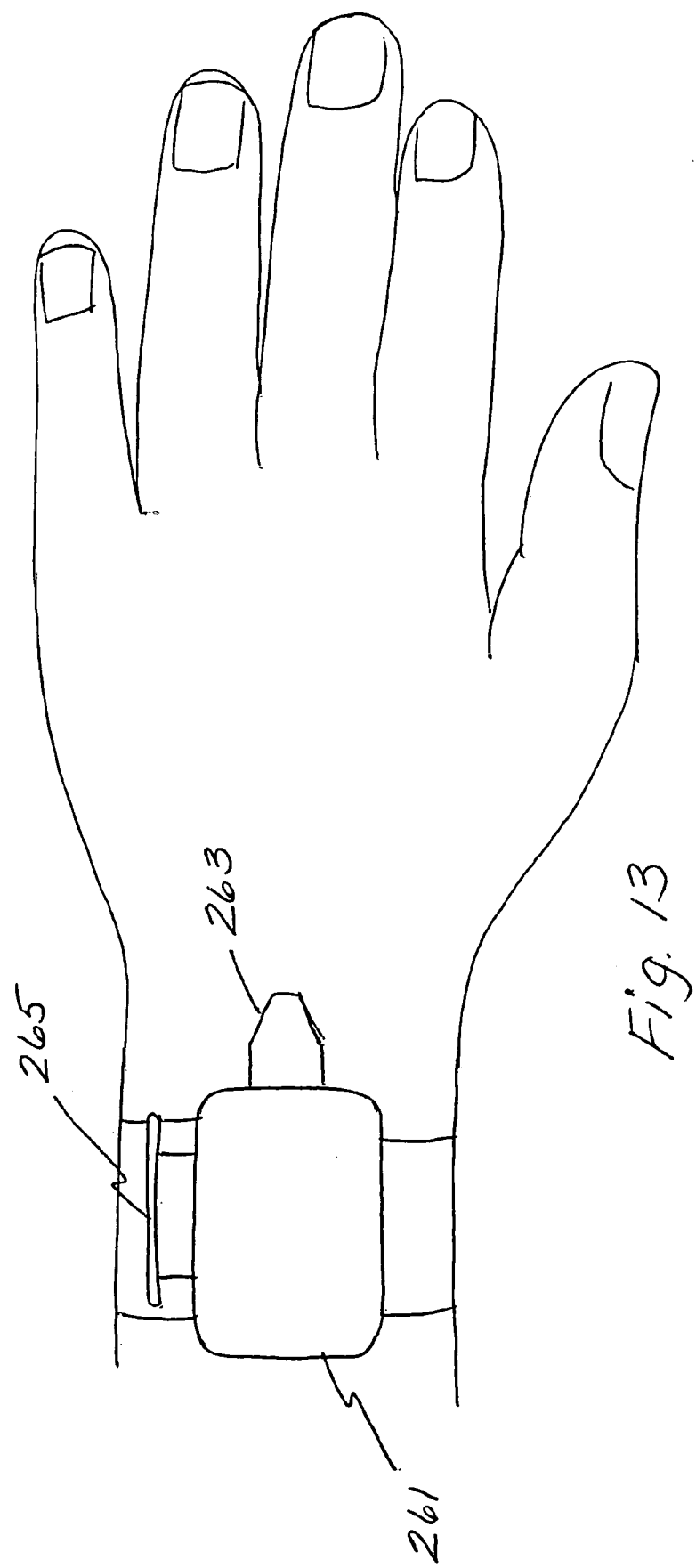

Wrist Mounted Hand Sanitizer Dispenser
Concept A

Wrist Mounted Hand Sanitizer Dispenser
Concept B

Wrist Mounted Hand Sanitizer Dispenser
Concept C

Refillable or disposable

Wrist Mounted Hand Sanitizer Dispenser

Concept D

Clear windows allows user to see remaining sanitizer

Wrist Mounted Hand Sanitizer Dispenser
Concept E

Replacement Tube

Each ratchet click expels one dosage of sanitizer

Wrist Mounted Hand Sanitizer Dispenser

Concept G

Molded in tongue compresses packet when pressed

Replaceable sanitizer packet is punctured when inserted

Sanitizer exit

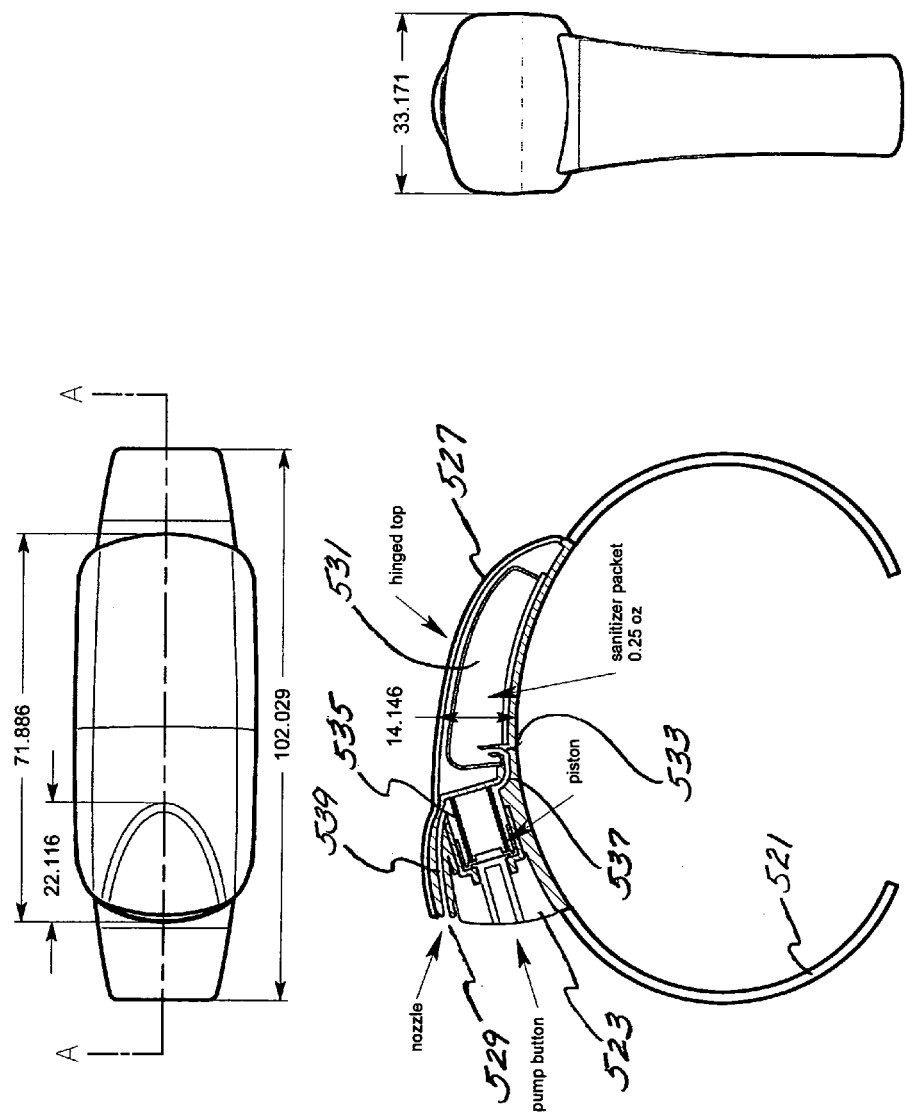

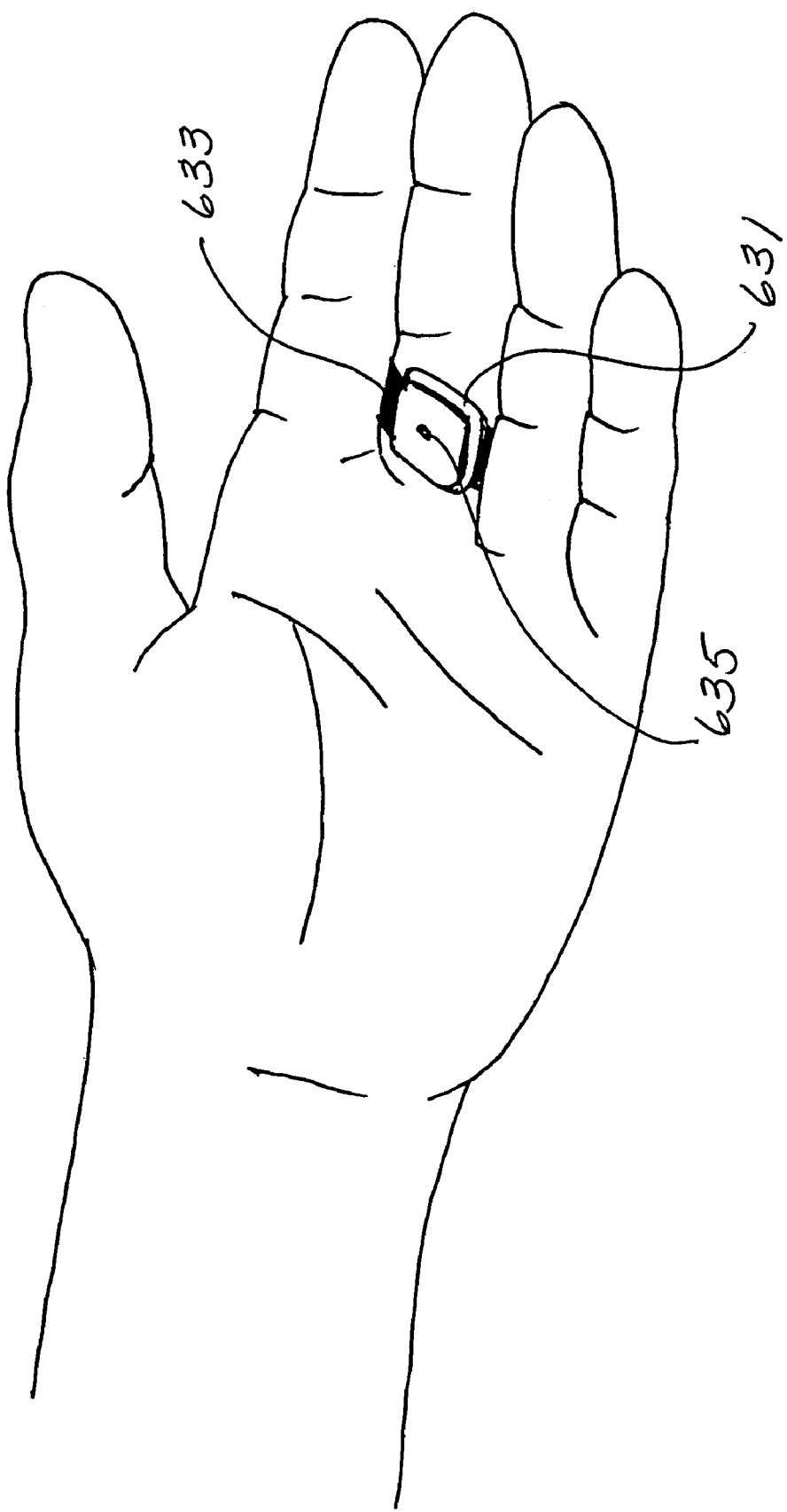

PORTABLE DEVICE FOR DISPENSING SKIN TREATMENTS

REFERENCE TO RELATED APPLICATION

This application is a continuation-in-part of application Ser. No. 10/314,825, filed Dec. 9, 2002, now abandoned. The present application claims the benefit of U.S. Provisional Application Nos. 60/515,718, 60/515,775, 60/515,793, and 60/515,794, all filed Oct. 30, 2003 as well as Disclosure Document No. 524,065 filed Jan. 4, 2003, Disclosure Document No. 525,532 filed Feb. 5, 2003, Disclosure Document No. 534,422 filed Jul. 7, 2003, and Disclosure Document No. 536,414 filed Aug. 8, 2003.

BACKGROUND—PRIOR ART

The increase in bacterial immunity to modern antibiotics is problematic and one of the chief vectors of infection is the human hand. Hence, when not in the proximity of a washroom to disinfect one's hands, it would be useful to have a means to accomplish such sanitation. Also, in the midst of daily activities, it can be inconvenient to uncap bottles of disinfecting gels or hand lotions to otherwise treat the hands.

Fortunately, it has been established that ethyl alcohol is a most effective antiseptic for gram-negative pathogens; it is of low viscosity, easily dispensed from a portable container, and does not require the use of a material wipe or cloth because of the speed of evaporation. Further, an adequate dose for sanitizing the hands comprises but a few drops of this antiseptic. To prevent chafing, glycerin can be added to the alcohol without levels of viscosity increase that would be deleterious to the dispensing process.

Various methods of portable disinfectant or lotion dispensers have been disclosed in the prior art. These include body-mounted dispensers, wrist bracelet dispensers, and others. U.S. Pat. No. 6,371,946 discloses a dispensing tube that drips liquid onto the hand. U.S. Pat. No. 6,053,898 discloses a tube-fed finger dispenser. A body-worn dispenser of form factor similar to a pager is disclosed in U.S. Pat. No. 5,927,548.

What has not been demonstrated is a dispenser that is wrist- or arm-worn that provides ease of actuation and, more specifically, single hand actuation. Neither has there been a device that can be surreptitiously actuated. This is an important consideration with respect to public relations. Individuals such as business and sales personnel may come in contact with and greet many people during the day. It would be desirable to have the option of sanitizing the hands after a handshake with a person without conveying a disdainful message to that person in so doing.

A wrist-mounted dispenser that achieves dispensing directly to the hand with a simple hand action is a major advantage of the present invention. This is especially useful to nurses and doctors in busy hospital settings, as well as for allied healthcare workers who cannot take time to repeatedly wash their hands with soap and water. With the advent of new forms of communicable disease such as SARS, an important consideration regards means to prevent disease spread. In this vein, the present invention provides a dispensing modality for viricidal and antibacterial prophylactic treatments of the hands and other exposed parts of the body.

SUMMARY OF THE INVENTION

The present invention discloses a wrist- or forearm-mounted device for dispensing a small amount of alcohol-based disinfectant hand rub, moisturizer, or other hand medicament. Even powder-based hand treatments can be dispensed using the present invention. A wristband or other attachment means affix the device to arm or wrist. Various locations are feasible including the top, side, or underside of the wrist or forearm. One embodiment provides for a finger-mounted geometry. In a preferred embodiment, the device is in the form of a low profile, wrist-mounted dispenser with a nozzle that produces a small amount of dispensed skin treatment when actuated. In an advanced embodiment, the dispenser is of a pressure multiplying design that shoots a single "dose" of liquid under pressure when mildly actuated by the fingers of the hand. Surreptitious actuation and dispensing of hand treatments is made possible with embodiments of the invention that are mounted on the underside of the wrist and can be easily actuated in a causal, not easily detected manner.

Because only a few drops of alcohol-based disinfectant comprise a dose adequate to achieve sanitation of the hands, the device of the present invention can dispense hundreds of doses of disinfectant before requiring refill or disposal. It can be used at any orientation of the arm and will avoid leakage when not actuated. Options exist for the fabrication of the device whether disposable or refillable. For example, hard or soft pliable plastics can be employed and even biodegradable materials can be used for disposable versions. Various embodiments of the invention include different mechanical designs for actuation and nozzles, dispensers detachable from wristbands, cartridge-based dispensers, dispensers with functioning watch faces, hybrid watch-dispensers, and methods of mounting to the top, side, or underside of the wrist or arm.

OBJECTS AND ADVANTAGES

Several objects and advantages of the present invention are:
(a) Provide a convenient, portable means for dispensing hand treatments;
(b) Provide a cost-effective means for dispensing hand treatments;
(c) Provide an unobtrusive means for dispensing hand treatments;
(d) Provide an easily actuated means for dispensing hand treatments;
(e) Provide an arm- or wrist-mounted means for dispensing hand treatments;
(f) Provide a wrist-mounted disposable means for dispensing hand treatments;
(f) Provide a cartridge- or packet-based means for dispensing hand treatments;
(g) Provide a hand treatment dispenser with wristwatch functionality.

BRIEF DESCRIPTION OF THE DRAWINGS

FIG. 1a is a pictorial diagram of the basic form of a dispenser mounted on the top side of the wrist.

FIG. 1b is a pictorial diagram of articulation of the hand to receive hand treatment dispensed from the device of FIG. 1a.

FIG. 2 is a pictorial diagram of the basic form of a dispenser mounted on the under side of the wrist.

FIG. 3a is a pictorial diagram of a dispenser exhibiting a refill port and actuation area mounted on the under side of the wrist.

FIG. 5a is a pictorial diagram of dispenser detachable from a wristband.

FIG. 5b is an end view of a dispenser of FIG. 5a attachable to a wristband using Velcro.

FIG. 5c is a pictorial view of snaps used to attach a dispenser of FIG. 5a to a wristband.

FIG. 6c is a plan view of components of the nozzle assembly of the pressure-multiplying squeeze dispenser.

FIG. 6d is a pictorial view of the hidden components of the nozzle assembly of the pressure-multiplying squeeze dispenser.

FIG. 10 is a cross-sectional view of an adjustable nozzle.

FIG. 11 is a pictorial view of a dispenser with a flow-adjusting nozzle.

FIG. 12a is a pictorial view of a detachable plunger-based dispenser with the plunger motion collinear with the fluid ejection axis.

FIG. 12b is a perspective view of the dispenser of FIG. 12a.

FIG. 12c is a pictorial view of the dispenser having a cap.

FIG. 13 is a pictorial view of a plunger-based dispenser having the plunger oriented perpendicular to the fluid ejection axis.

FIG. 26b is a cross-sectional view of the dispenser of FIG. 26a.

FIG. 30 is a pictorial diagram of a dispenser mounted to a finger of the hand.

Figure 1B:
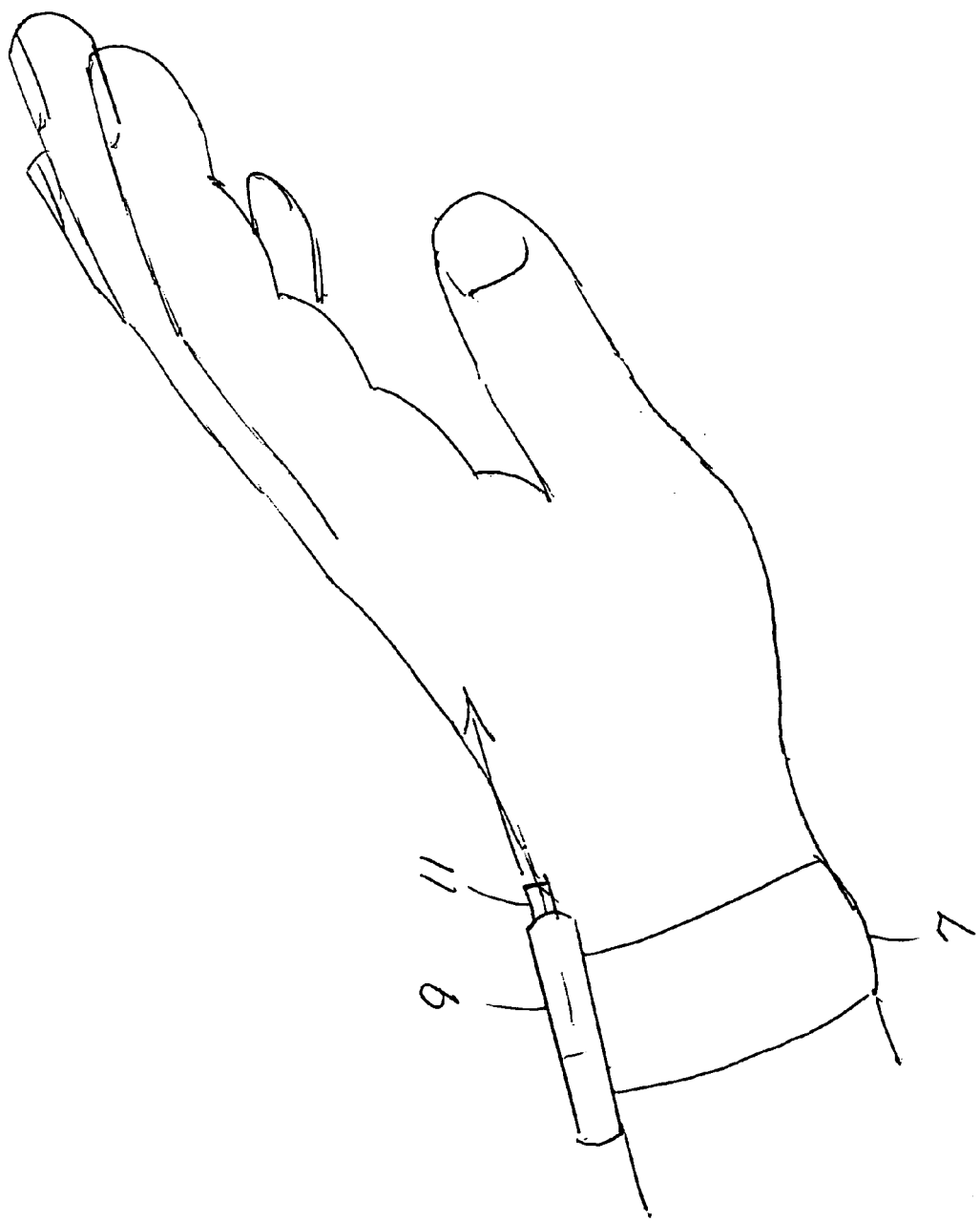

The following definitions serve to clarify the disclosed and claimed invention:

Bladder refers to an elastic, resilient container that can be deformed under compression.

Pressure-multiplying refers to those devices relying on the technique of increasing, by mechanical advantage, the compression pressure of a working fluid. This is achieved by use of an ejection fluid-containing tube that penetrates an ejection fluid-containing piston under the influence of the working fluid.

Hand treatment material comprises any of a host of liquid, powder, gel, or aerosol medications, or sanitizing agents that are topically applied to the hands. Examples include alcohol, glycerin, moisturizing lotions, and desiccating powders.

Working fluid refers to the fluid which transfers manual pressure to the material to be dispensed. Such transfer of pressure can occur in one or multiple stages and typical working fluids include air contained in a squeeze bottle as well as liquid versions of the hand treatment material itself.

DETAILED DESCRIPTION OF THE INVENTION

The present invention is useful for dispensing either hand treatments such as moisturizers or disinfectants; even powders can be dispensed in powder-aerosol form. Typically, the active ingredient in hand antiseptics such as Purel™ is ethyl alcohol. This is fortuitous because it is a relatively non-toxic liquid that exhibits low viscosity over the temperature range of interest for this application. This makes delivery of a directed stream of fluid relatively easy. In contrast to liquid, alcohol gels are useful in that they do not run and although they will require more force to dispense than liquid, such higher viscosity disinfectant or moisturizing formulations can be accommodated in differing embodiments of the present invention. Various means of dispensing the aforementioned hand treatments are feasible and can be tailored to the type of material to be dispensed. The target locations for deposition of the hand treatment include the regions on the top of the hand, and the underside of the hand, either fingers or palm. The preferred embodiment for a means of dispensing hand treatment dosages is a device that attaches to either the top or underside of the wrist. Such a device can be worn unobtrusively underneath a long-sleeved shirt.

Various approaches can be used to create the fluid dispenser. In a simple squeeze compartment design, a bladder reservoir expels fluid upon application of pressure to the bladder. In a plunger-based design, a syringe-type plunger causes the fluid in a reservoir to be expelled upon application of force to the plunger. Spray or squirting mechanisms analogous to squirt guns use a more specialized plunger mechanism and include a nozzle. A drip system would rely on gravity feeding of the liquid through some orifice for delivery to the hand. More elaborate schemes include use of a prime mover such as a miniature electrical actuator or pump.

Following is a taxonomy of dispenser types identified:

Squeeze
  simple compression
  pressure-multiplied compression
Plunger
  simple plunger
  pressure-multiplied plunger
  same hand-actuated
Drip
Gas Pressurized
  disposable
  gas cartridge
Pump
  thermoelectrically-heated working fluid
  electromechanical
Remote Control—low power radiofrequency, single chip receiver
Basic Configuration There are two fundamental approaches to dispensing hand treatment. In one approach, the hand treatment is dispensed to the hand of the arm upon which the dispenser is mounted. Actuation of this dispenser can be by either hand. In the second approach, the hand treatment is dispensed to the hand of the arm or other body part which does not have a dispenser attached. In this case, it is also true that actuation of the dispenser can be by either hand. The various embodiments discussed below will use one of these two approaches. Typically, hand treatment material will be ejected either parallel or perpendicular to the longitudinal axis of the forearm. In a preferred embodiment that uses the second aforementioned approach, the hand treatment material is ejected perpendicular to the longitudinal axis of the arm upon which the dispenser is mounted.

The simplest reduction to practice would be a low profile bladder, with associated orifice or nozzle for ejection of hand treatment, mounted on the wrist. FIG. 1a depicts a hand treatment dispenser 1 having an aperture or nozzle 5 for dispensing hand treatment material to a surface of the hand. It is shown mounted to the top side of the wrist by means of a strap 3. The dispenser is characteristically actuated by compression of the bladder comprising the dispenser. Details of its construction and various embodiments are discussed below. FIG. 1b depicts the slight upward articulation of the hand about the wrist that is conducive to dispensing treatment from nozzle 11 to the top of the hand upon compression of dispenser 9 attached to wristband 7. FIG. 2 depicts the dispenser 13 mounted by strap 15 to the underside of the wrist for dispensing of treatment to the palm of the user's hand by way of nozzle 17. Mounting to the underside of the wrist provides a more covert implementation, especially if worn under a long-sleeved shirt or blouse.

The dispenser can be removably attached to the wristband so the user can mount it to the top, side, or bottom of the wrist to suit the user's desire. Various attachment schemes including Velcro, snaps, and other methods, as well as various nozzle configurations that are compatible with these various mounting schemes are discussed in detail below.

Figure 3B:
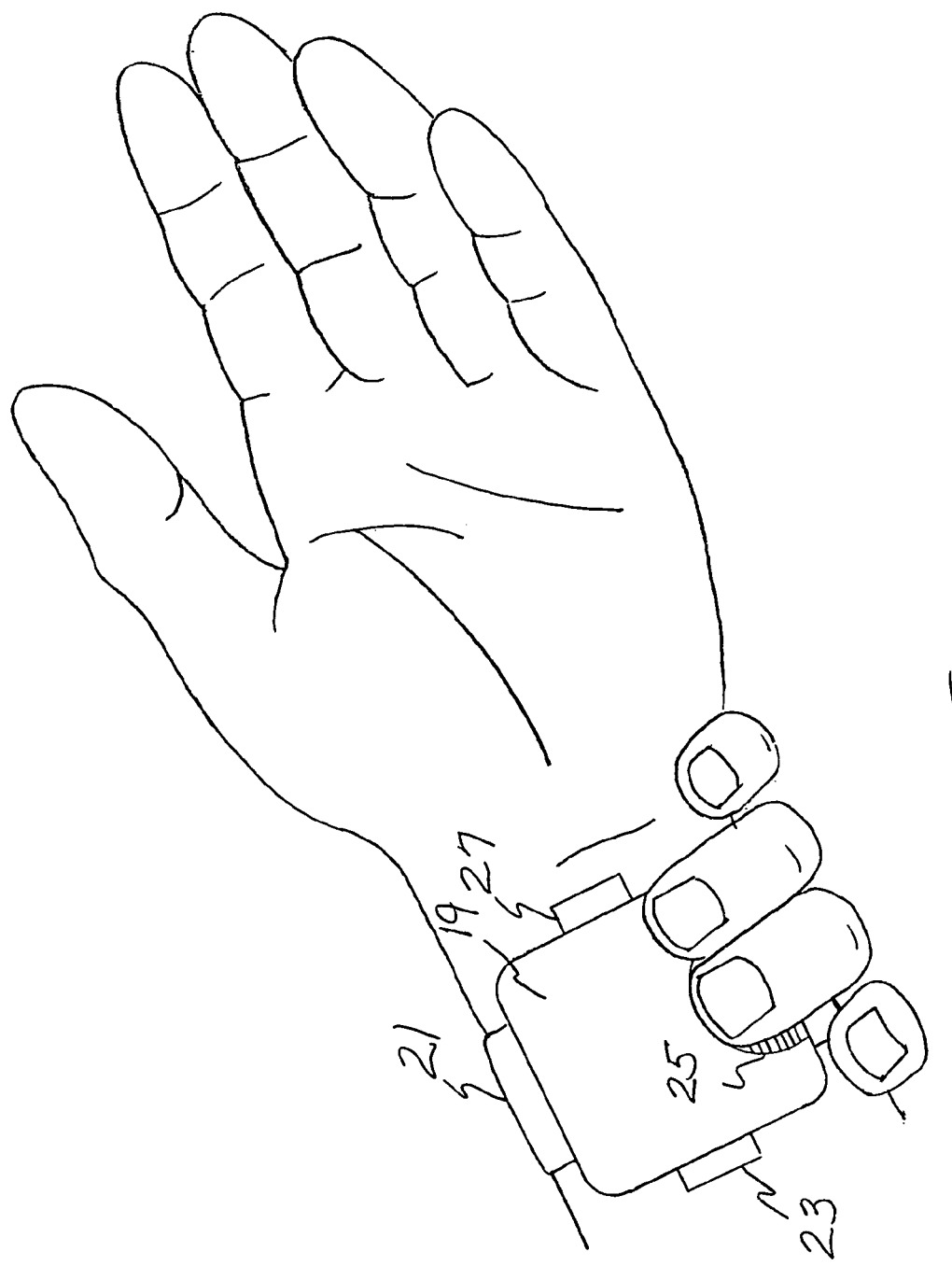
FIG. 3b is a pictorial diagram of the dispenser of FIG. 3a showing a convenient method of actuation.
Figure 4:
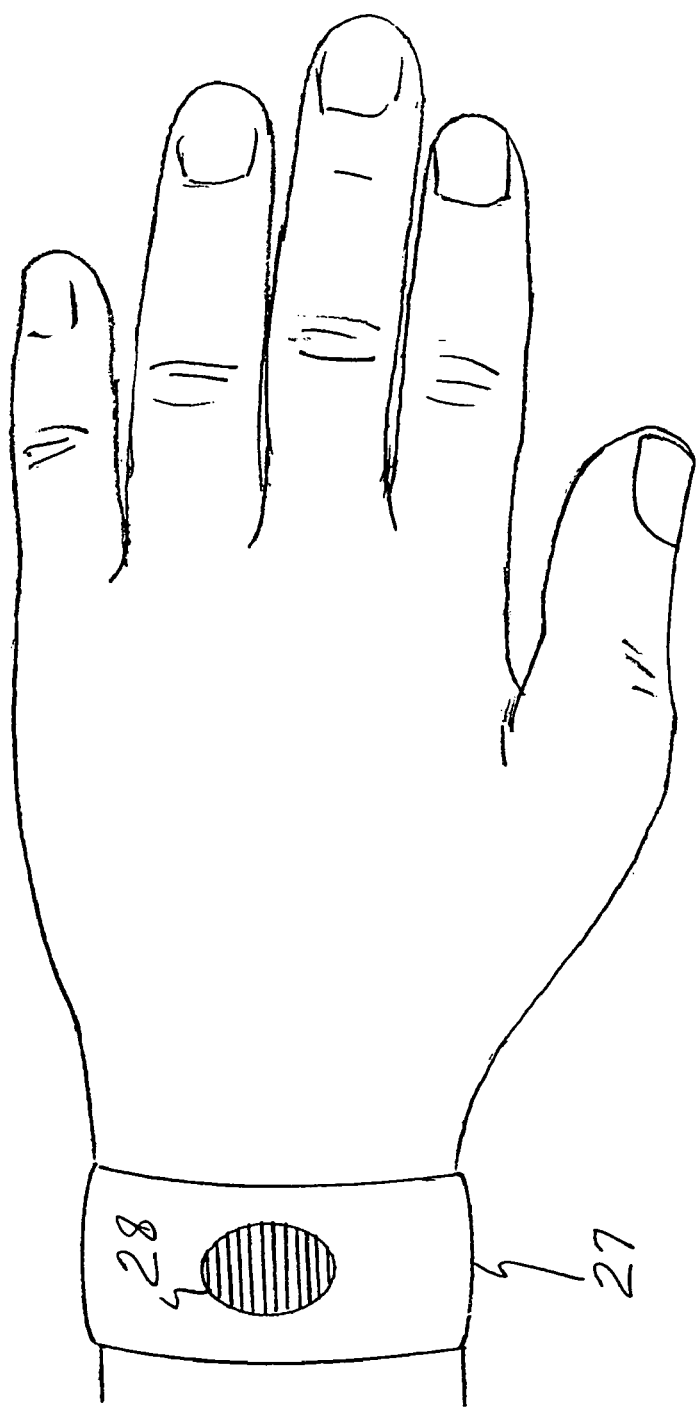
FIG. 4 is a pictorial diagram of a hand treatment fluid-filled wristband usable with a dispenser such as that of FIG. 2.

A refinement of the device of FIG. 2 is depicted in FIGS. 3a and 3b showing a thin bladder 19 mounted on the underside of the wrist by wristband 21. The device is shown to have a nozzle assembly 27 and, optionally, a capped refill aperture 23. A finger depression area 25 is highlighted. Alternatively, the wristband itself can be part of the dispenser as shown in FIG. 4. A working fluid whether air or liquid can fill a portion or all of the wristband 27. Upon depression of the area 28 atop the wristband, pressure can be conveyed to the dispensing bladder underneath the wrist to cause a stream to be ejected into the hand. This can be especially effective by means of the pressure-multiplying dispenser discussed below. A three-dimensional depiction of the dispensing bladder is provided in FIG. 5a. The bladder 31 can be formed from soft, pliable plastic such as polyethylene or other plastic not attacked by the chemical constituents of the hand treatment. A nozzle assembly 32 is shown with a centrally-located nozzle aperture 33. The bladder 31 can be made integral with the wristband 30 or as shown in FIGS. 5b and 5c, made attachable to the wristband. In FIG. 5b, the bladder 31 is shown attachable to the wristband 30 by VELCRO hook and pile material [Velcro] component strips 34 and 35. FIG. 5c depicts the use of snap elements 36 on the wristband 30 that mate with the snap element counterparts on the side of the bladder. Another approach is to use clips that would attach to a wristwatch band.

Figure 6A:
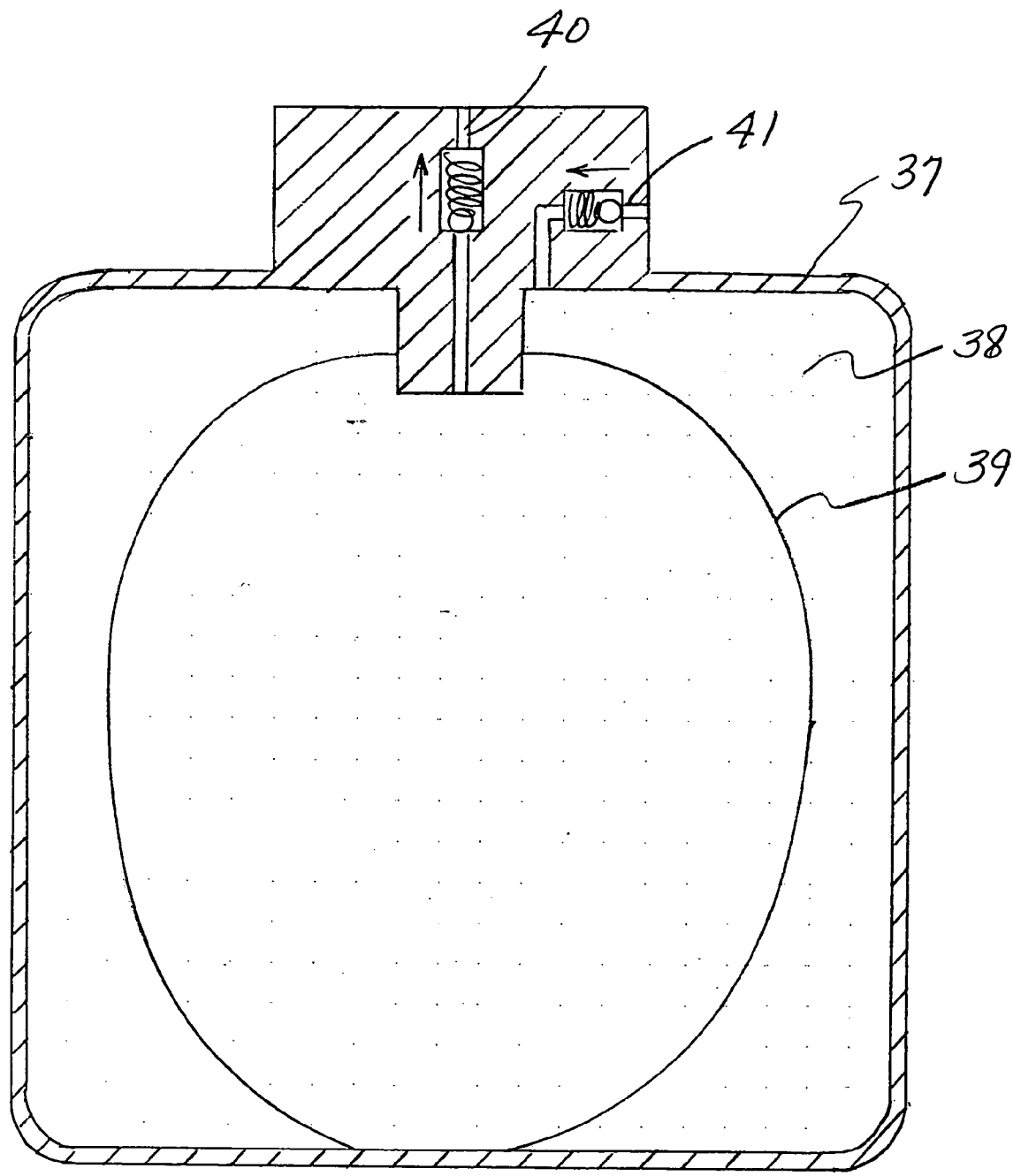
FIG. 6a is a cross-sectional view of a basic squeeze dispenser.

FIG. 6a is a cross-sectional view of a simple embodiment comprising a squeeze bottle 37. Internal to the squeeze bottle 37 are shown an air volume 38 and a hand treatment material-filled pliable bladder 39. Upon squeezing bottle 37, the pressure of air volume 38 is conveyed to material-filled bladder 39 so that the material is ejected from check valve-controlled channel 40. The check valve in this channel prevents leakage, but allows ejection of hand treatment material under pressure. Upon release of pressure to bottle 37, air is allowed to enter check valve-controlled channel 41 so as to replace the volume of hand treatment material ejected. The segregation of air and hand treatment material volumes permits the use of the device at any orientation with respect to gravity.

Pressure-Multiplying Squeeze Dispenser

A more sophisticated embodiment of the invention makes use of a pressure-multiplying squeeze dispenser. Such a dispenser provides relatively high pressure ejection of fluid upon application of relatively little manual pressure. This allows good fluid stream formation and control over the stream trajectory to the target hand. For this reason, U.S. Pat. Nos. 4,4603,794 and 5,289,948 are hereby incorporated by reference thereto. In the first of these patents, the fundamental concept of a pressure-multiplying piston is disclosed. A pressure amplification is achieved that is equal to the ratio of the cross-sectional area of the pressure-multiplying piston to the cross-sectional area of a tube penetrating the pressure-multiplying piston.

Figure 6B:
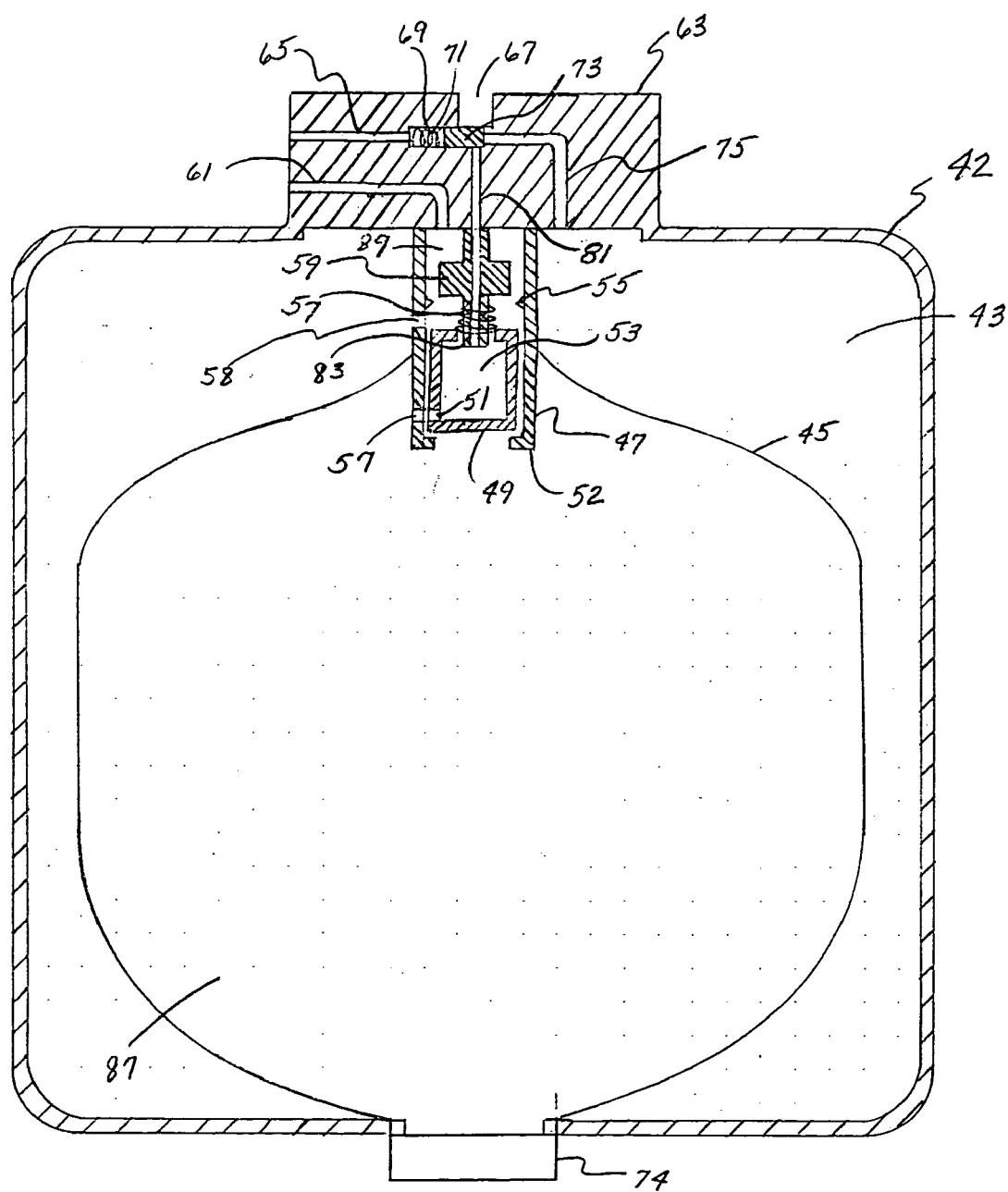
FIG. 6b is a cross-sectional view of a pressure-multiplying squeeze dispenser.

Necessary to the present invention is means to allow the dispenser to operate independent of its orientation with respect to the gravity field and the need to insure leak-proof operation. The pressure multiplying concept is adapted to the present invention to achieve these goals as shall be described with reference to FIG. 6b, a cross-sectional view of a pressure-multiplying version of the present invention. Shown is an outer bladder 42 having an output nozzle assembly 63 and a refill port with cap 74. Interior to the bladder 42 is an even more pliable bladder 45 that segregates the volume of the bladder 42 into an air-filled space 43 and a fluid-filled space 87. As can be appreciated, this is for the purpose of allowing operation independent of orientation with respect to gravity, in the same fashion as the embodiment of FIG. 6a. Upon compression of bladder 42, air in volume 43 causes compressive pressure on fluid-filled bladder 45. This pressure is transferred to fluid-filled movable cylinder 49 which translates within an outer guide cylinder 47. Cylinder 49 has been filled with fluid by virtue of port 51 on the side of cylinder 47 near its base. As cylinder 49 is caused to translate upward, port 51 is sealed by the wall of cylinder 47 so that the pressure of fluid 53 inside cylinder 49 is applied to the end of tube assembly 83. Similarly, as cylinder 49 begins upward translation, air intake port 58 is sealed by the wall of cylinder 49 so that air in volume 89 is exhausted through channel 61. The pressure of the fluid in channel 81 of tube assembly 83 is increased over the pressure of the fluid in bladder 45 by the ratio of the cross-sectional area of cylinder 49 to the cross-sectional area of the end of tube assembly 83.

As cylinder 49 travels upward against the preload provided by spring 57 which is in turn captivated by spring seat 59, the air in volume 43 opens spring-loaded gate valve assembly 73 so as to allow fluid to be ejected from channel 81. Retaining protrusions 55 on the inside wall of cylinder 47 limit the upward travel of fluid-filled cylinder 49 in dispensing of a single dose of hand treatment. After the maximum amount of fluid in volume 53 of cylinder 49 is ejected at the limit of travel for cylinder 49 and upon removal of actuation pressure to bladder 42, cylinder 49 under spring tension travel back downward into bladder 45. Retaining flange 52 limits the downward travel of cylinder 47. As cylinder 49 descends, its interior is under a partial vacuum and upon exposure of port 51 to the fluid in volume 87 by way of port 57 in the wall of cylinder 47, the interior of cylinder 49 is refilled with liquid. At this same time, air intake port 58 in the wall of cylinder 47 is opened to allow air to enter volume 43 by way of volume 89 and channel 61.

FIGS. 6c and 6d serve to illustrate the function of gate valve assembly 73. In FIG. 6c, it can be observed that the gate valve assembly 73 is actually a mechanism with three forward prongs and one backward-directed extension held in a position which blocks fluid channel 81 by means of preload spring 71. The central forward prong has a rectangular or square cross section in contrast to the circular cross sections of the other prongs and the backward-directed extension so as to seat over the top of channel 81. Air pressure to displace the gate valve assembly 73 and open fluid channel 81 is applied only to the two outboard prongs of assembly 73 by way of air channels 75. Upon displacement of gate valve assembly 73, it occupies additional volume 77. Air channel 65 provides for release of air from spring compartment 69 upon progress of the backward-directed extension of assembly 73 into compartment 69.

Plunger-Type Dispenser

Figure 7:
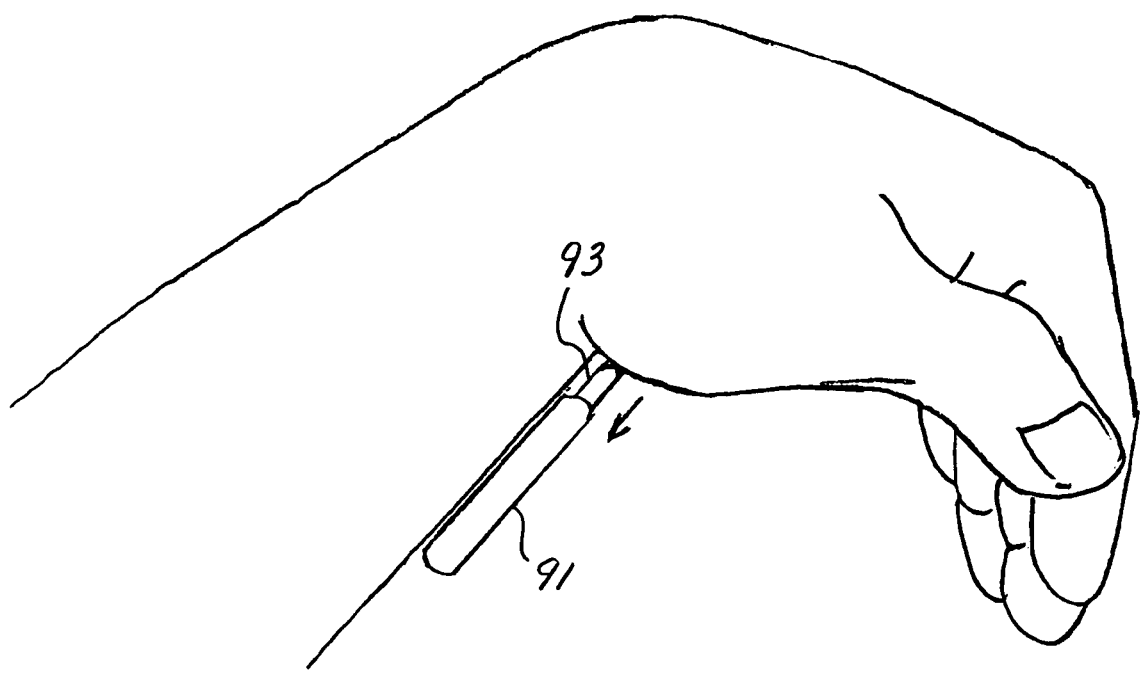
FIG. 7 is a pictorial view of the wrist motion actuation of a plunger-based dispenser.

An alternative to squeeze dispensing makes use of a plunger. The way in which a plunger would be exploited in the present invention is shown in FIG. 7, a pictorial side view of such a plunger-based device. In this embodiment, a fluid storage compartment 91 of the same form factor as the previously described squeeze bladder is likewise mounted on the underside of the wrist. A fluid-dispensing plunger 93 is actuated by downward flexion of the hand at the wrist so as to depress plunger 93 with the base of the palm. With this motion, hand treatment fluid is ejected onto the base of the palm and both hands can be rubbed together to disperse the treatment.

Figure 8:
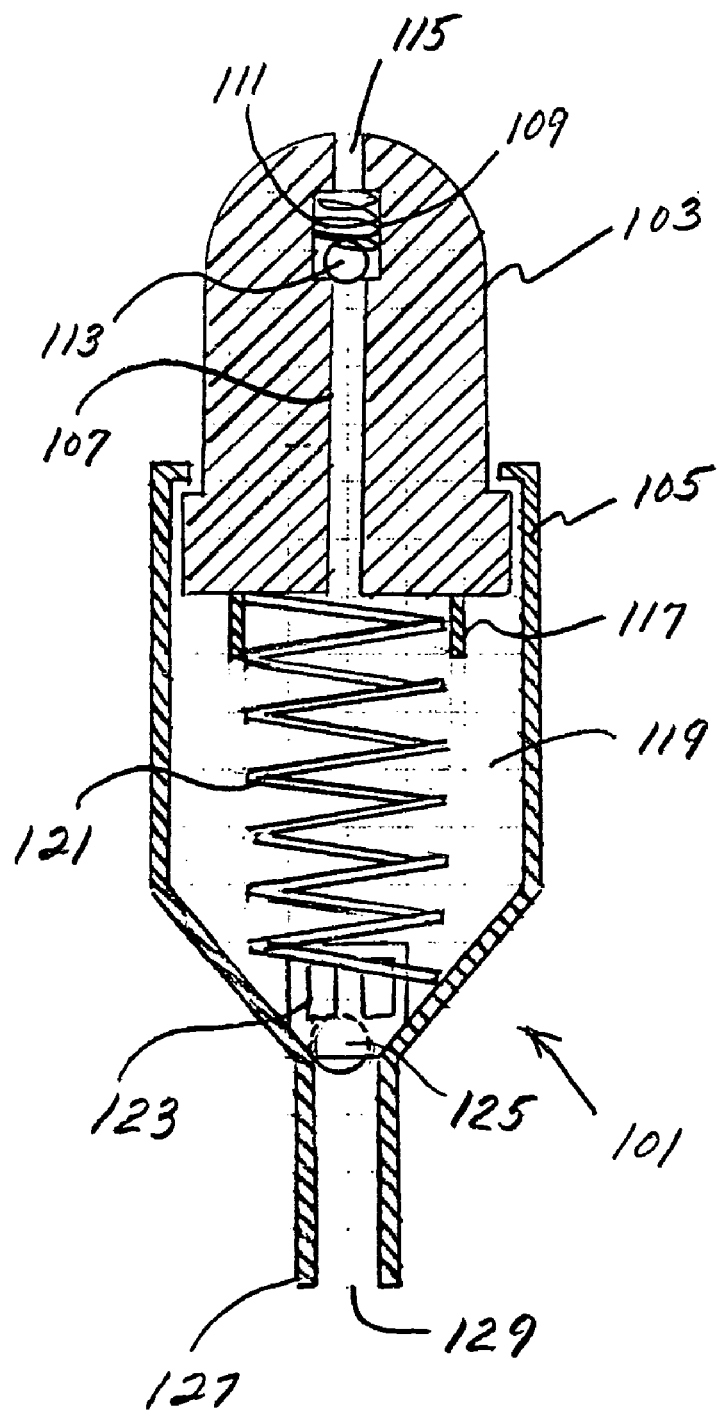
FIG. 8 is a cross-sectional view of a prior art plunger.

The type of plunger device 101 used on dish soap dispensers is shown in FIG. 8. A movable plunger 103 is spring loaded and captivated by housing 105. The preload spring 121 is seated against plunger 103 within cylinder 117. Tube 127 extends into fluid volume not shown. When the plunger 103 is depressed, air in volume 119 is impeded in downward flow by gravity check valve 125 having a cage 123 and is promoted in upward flow through channel 107 past spring loaded check valve 113. Upon release of plunger 103, a partial vacuum is formed in volume 119 which pulls fluid up through aperture 129 of tube 127 into volume 119 and onward up through channel 107 and out aperture 115. The tension of spring 109 is small, but sufficient to prevent unintended leakage of fluid. A miniature version of this plunger assembly can be fabricated for use as part of a plunger embodiment of the present invention.

Pressure-Multiplying Plunger-Type Dispenser

Figure 9A:
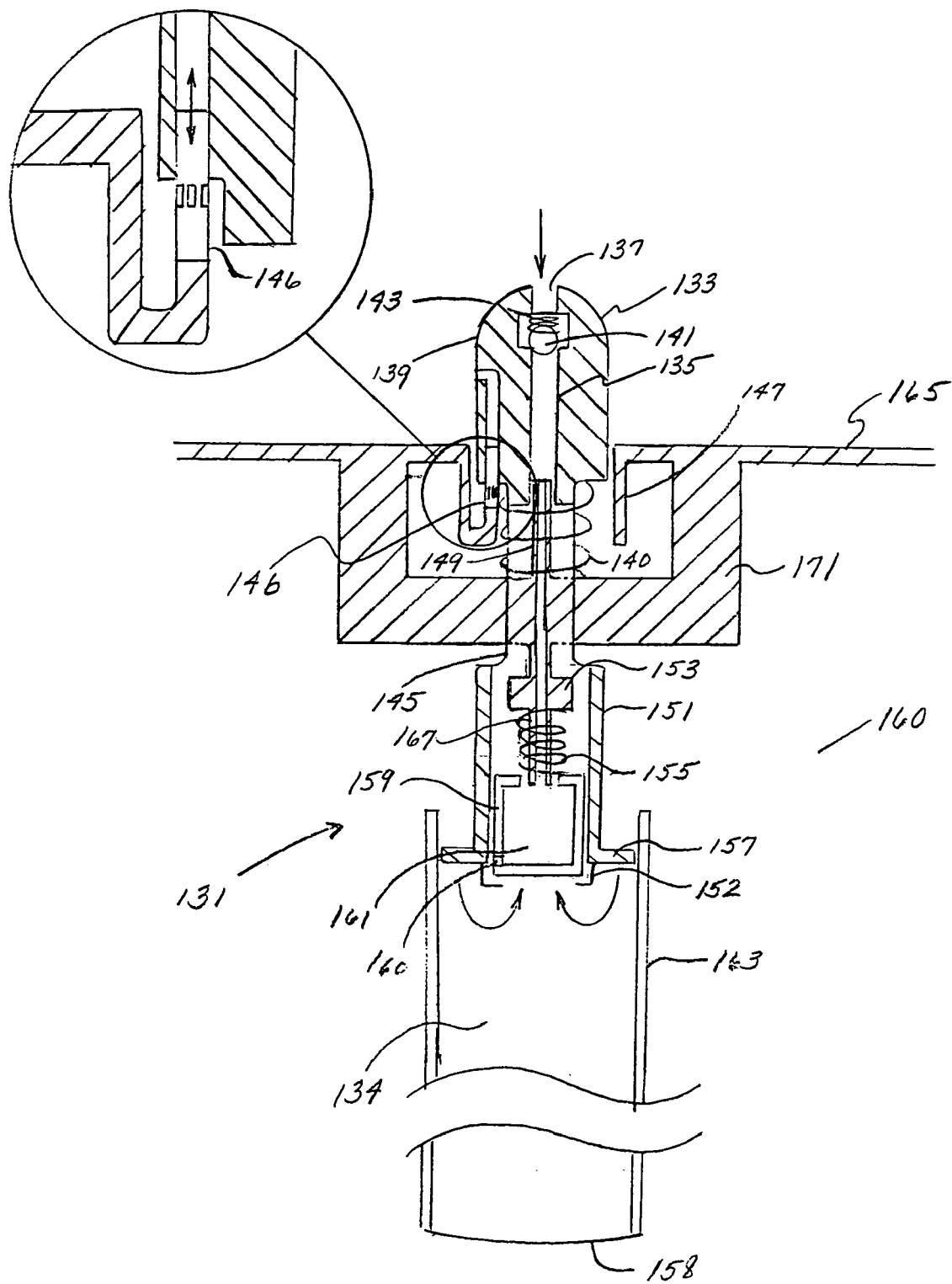
FIG. 9a is a cross-sectional view of a pressure-multiplying plunger dispenser.
Figure 9B:
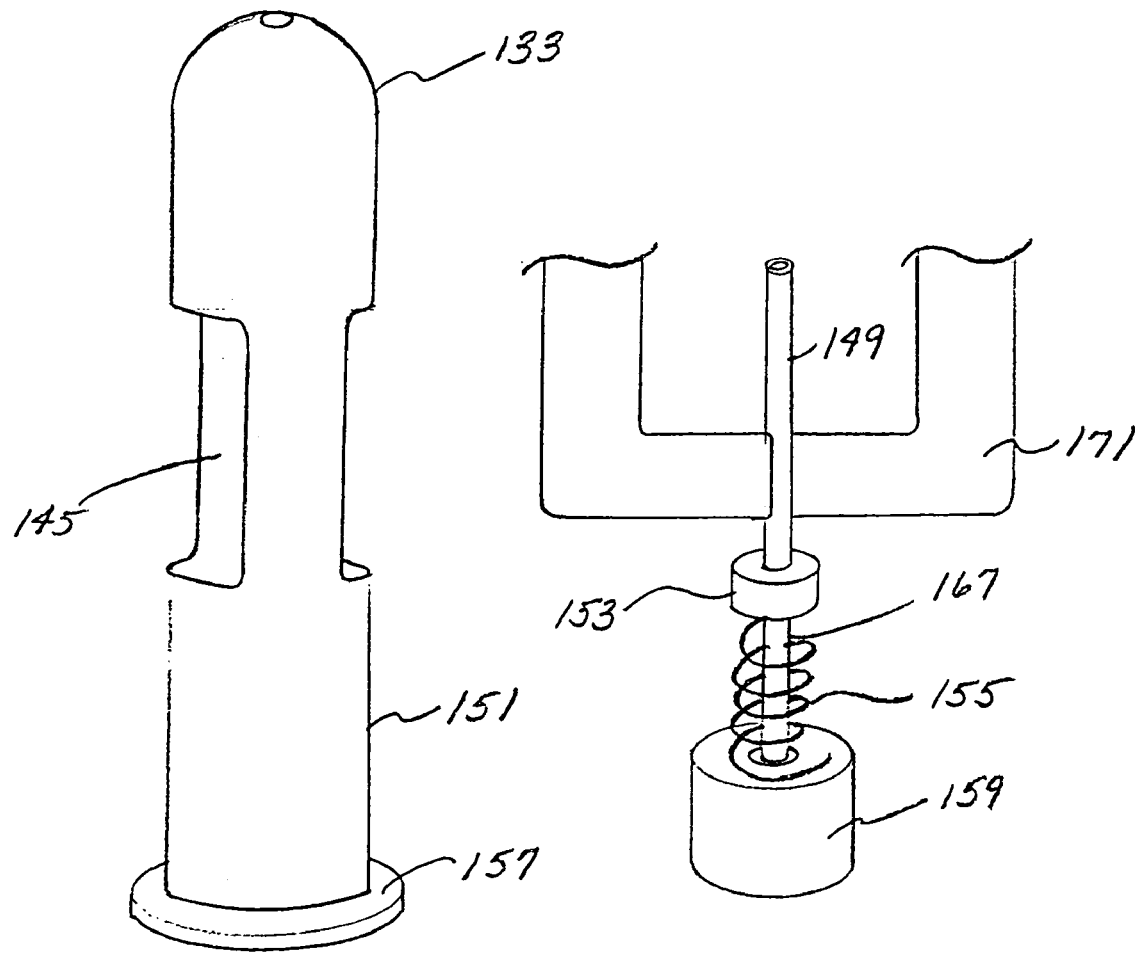
FIG. 9b is a pictorial view of components of the pressure-multiplying plunger dispenser.

Analogous to the pressure-multiplying squeeze dispenser is a pressure-multiplying version of the plunger device. A cross-sectional view of this device is shown in FIG. 9a. A movable plunger 133 has a preload tension from spring 140 that maintains its normal extended position. Spring 140 is seated against structural fins 171 internal to the dispenser. The plunger 133 has a central channel 135 that accepts the introduction of tube 149 connected by fins 171 to the dispenser housing 165, as plunger 133 is depressed. Cutouts 145 on the sides of plunger 133 admit the insertion of structural fins 171 which hold tube 149 in place. The lower portion of plunger 133 forms a cylinder 151 which houses a pressure-multiplying cylinder 159. Upon depression of plunger 133, the lower flange 157 of the plunger applies pressure to fluid volume 134 which in turn applies pressure to cylinder 159. This results in the upward travel of pressure-multiplying cylinder 159 and the high pressure ejection of fluid along channel 167 and channel 135, past check valve 141 and out through aperture 137. As the plunger 133 is depressed, the perforations of air intake tube 146 are sealed. Upon release of actuation pressure, plunger 133 returns upward by virtue of spring 140 and cylinder 159 returns downward under the influence of spring 155. Cylinder 159 refills with fluid as aperture 160 is in fluid communication with fluid volume 134. Near the limit of return travel for plunger 133, the perforations of air intake tube 146 are opened for air to refill volume 168. A flexible membrane 158 at the base of fluid container 163 allows air pressure in volume 168 to equilibrate with fluid pressure in volume 134. Retaining flange 152 limits the downward travel of cylinder 159. In FIG. 9b, the three-dimensional shape of plunger 133 is more clearly manifested. Shown are the cutout areas 145 which are penetrated by the structural fins 171 which hold tube 149 in fixed disposition with respect to the dispenser housing 165.

Nozzle Configurations

In the simplest embodiment, the nozzle of the present invention is of a fixed geometry. Other embodiments include retractable or extendible versions, as well as nozzles that can be adjusted in direction and those which allow selection of the output flow type from streaming to spraying. Adjustable nozzles can be implemented for pressure-multiplying dispensers with some increase in complexity over counterparts for non pressure-multiplying dispensers.

In various embodiments of the present invention, the nozzle will be oriented to provide unobstructed dispensing of hand treatment to the target hand. For the case in which hand treatment is to be dispensed to the hand of the arm upon which the dispenser is mounted, this can be accomplished even when the user is wearing a long-sleeved shirt or blouse, or a jacket. In situations where a garment might obstruct dispensing, it could be efficacious to have an extendible nozzle. An example of such a nozzle is shown in FIG. 10. A cylindrical nozzle body 201 is shown with ring embossments 203. A set of complementary ring depressions 205 is present in the neck 207 of the dispenser so that longitudinal motion of the nozzle body 201 relative to the dispenser neck 207 establishes a fixed number of detint positions.

As dictated by the preference of the user of the invention, the type of flow of dispensed material can be selected in an embodiment with flow control means. Numerous prior art examples of variable flow nozzles are extant in the patent literature; examples include U.S. Pat. Nos. 3,843,030, 3,967, 765, and 4,234,128. These nozzle designs exhibit variable flow geometry. An attending alteration in the flow from a streaming to spraying nature occurs upon rotation of one of the component members of the nozzle relative to the other. In FIG. 11, this type of nozzle is shown in the context of the present invention. A fixed nozzle component 223 is attached to the dispenser body 221. Rotation of the movable nozzle component 225 results in variation in the type of flow. In such an implementation, the flow channel is segmented into two portions and the alignment of a particular cross-sectional geometry of each of these portions of the channel is used to adjust the nature of the flow. Another method of varying the type of flow is that used in typical garden hose nozzles in which a flow output aperture is variably occluded by the longitudinal translation of a conical member with its apex directed into the flow output aperture by a screw motion.

Cartridge- and Pump-Based Embodiments of the Invention

Figure 14:
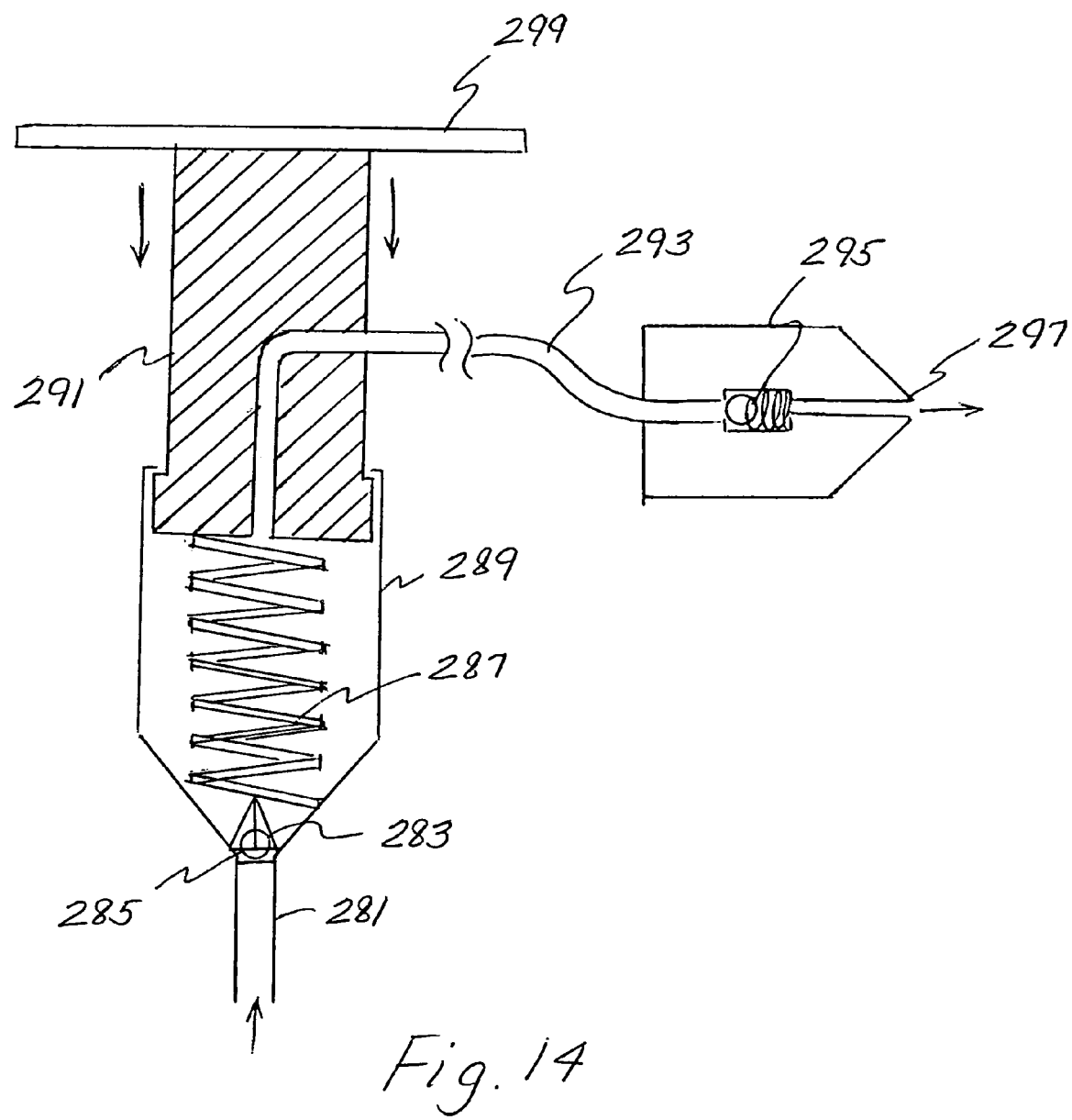
FIG. 14 is a cross-sectional view of the plunger and nozzle assembly of the dispenser of FIG. 13.

A dispenser detachable from a wristband is shown in FIGS. 12a through 12c. Depicted are wrist mounted, detachable, pump-based dispensers. FIG. 12a shows a pump spray type dispenser 241 mounted on top of the wrist. Flange 243 allows the depression of the end of the dispenser column to eject material from the nozzle 245. FIG. 12c depicts a detachable capped bottle. The cap 247 can be one which pops off, but is retained in connection with the dispenser by a plastic link. FIG. 13 depicts a pump spray bottle 261 in which the pump actuator flange 265 is mounted at 90 degrees to the axis of the spray nozzle 261. This can improve the ease of actuation by the fingers of the alternate hand. FIG. 14 depicts a naive means of implementing the dispenser of FIG. 13. When depressed, the actuation flange 299 with attached plunger 291 compresses spring 287 and reduces the free volume of plunger-containing body 289. Upon release of depressed actuation flange 299, the plunger 291 retracts creating a suction on inlet port 281 to intake fluid which fills plunger-containing body 289 and proceeds to travel through flexible tube 293 for ejection from nozzle 297. Check valves 283 and 295 prohibit deleterious flow of fluid.

Figure 15:
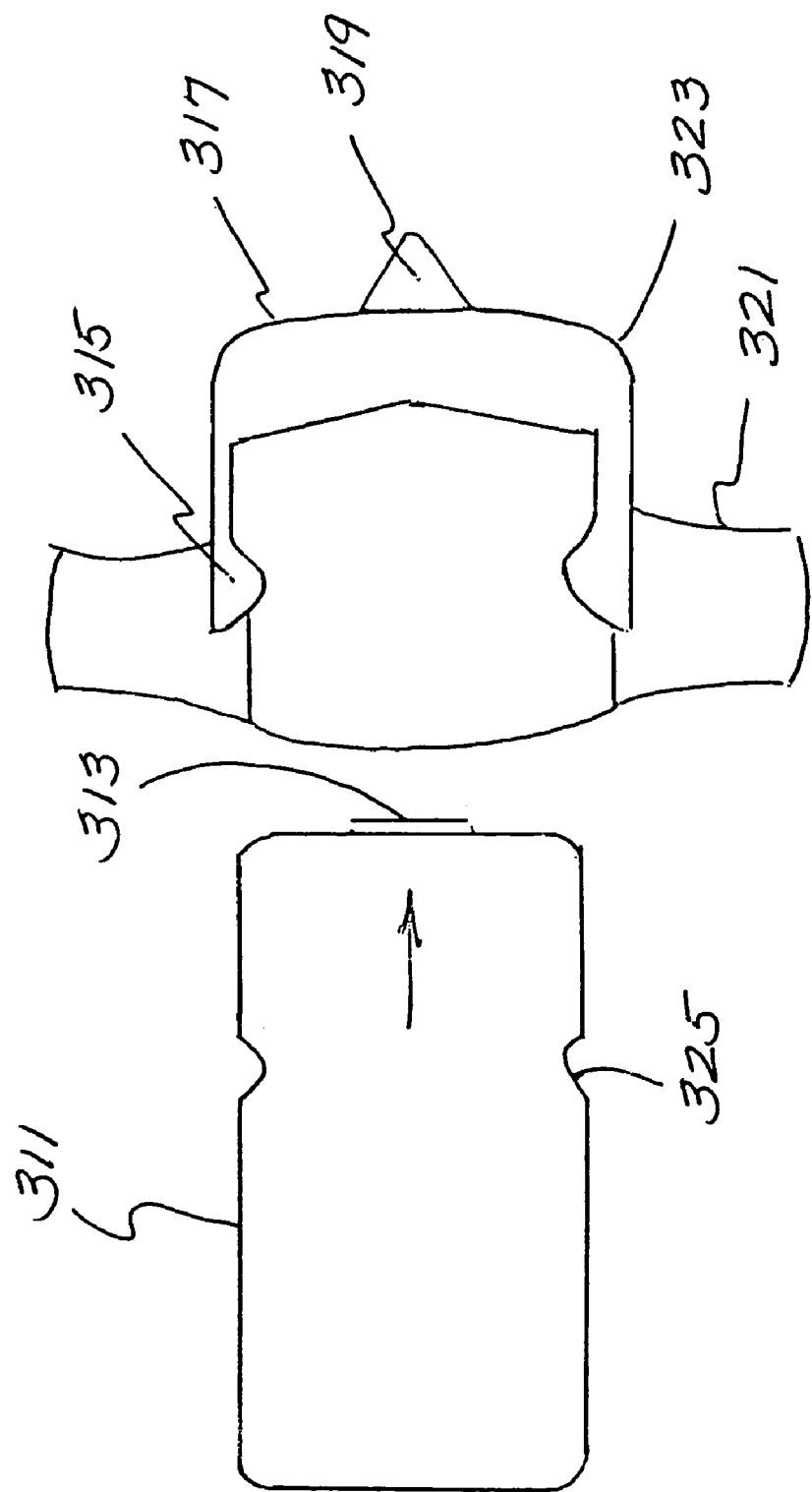
FIG. 15 is a pictorial view of a cartridge-based dispenser.
Figure 16:
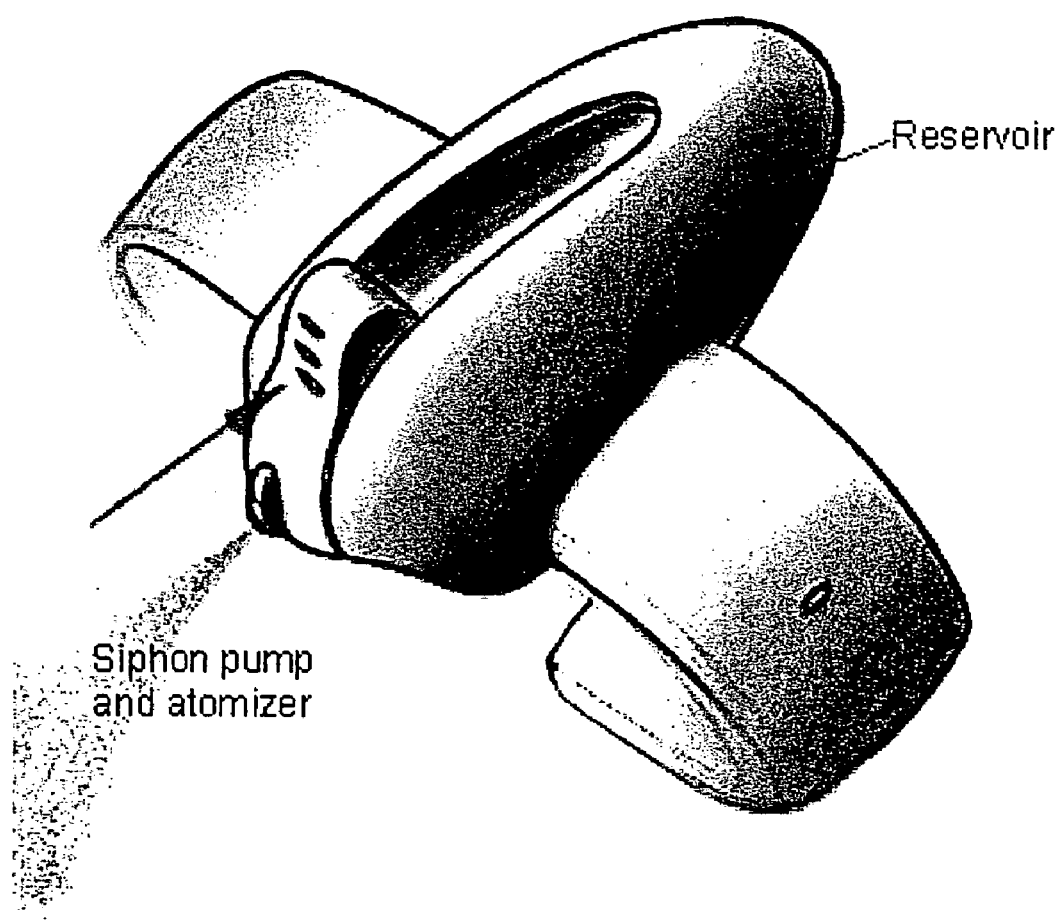
FIG. 16 is a pictorial view of a siphon pump-based dispenser ejecting fluid perpendicular to the longitudinal axis of the arm.
Figure 17:
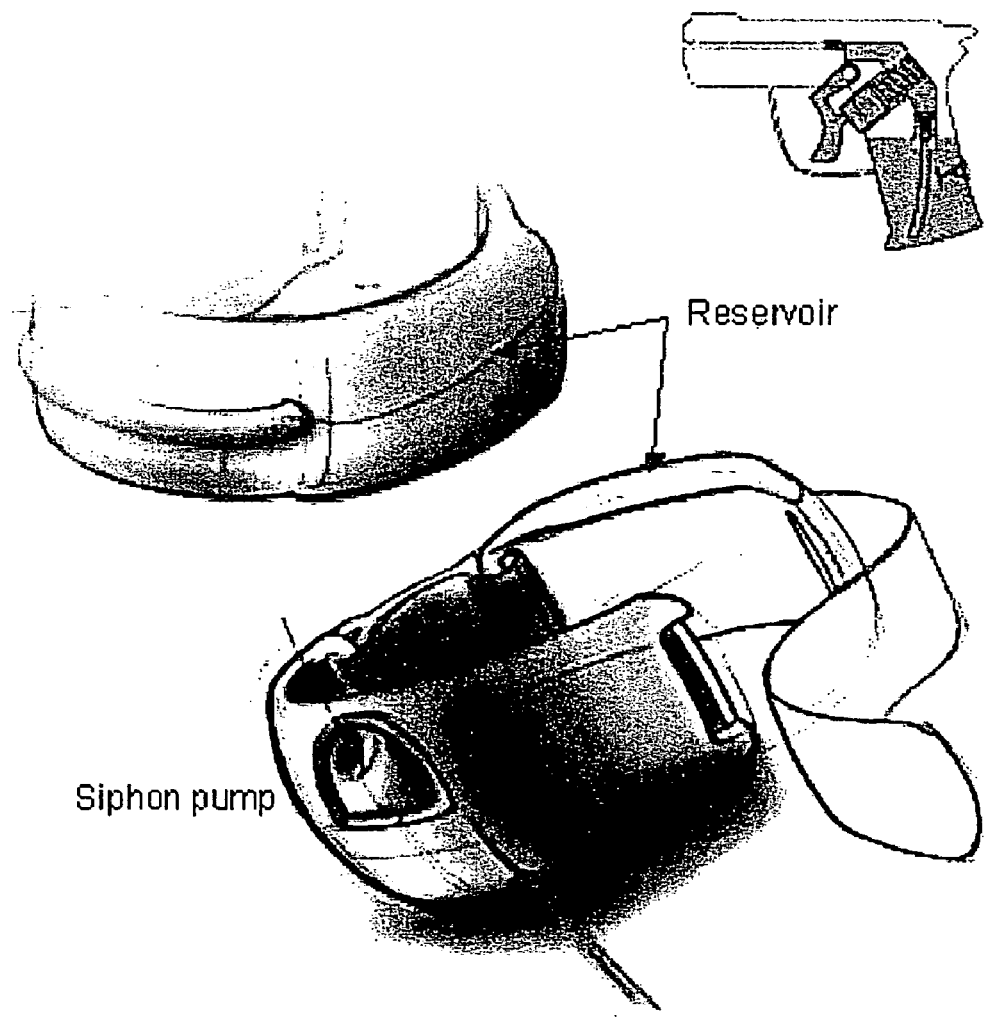
FIG. 17 is a pictorial view of a siphon pump-based dispenser ejecting fluid parallel to the longitudinal axis of the arm.
Figure 18:
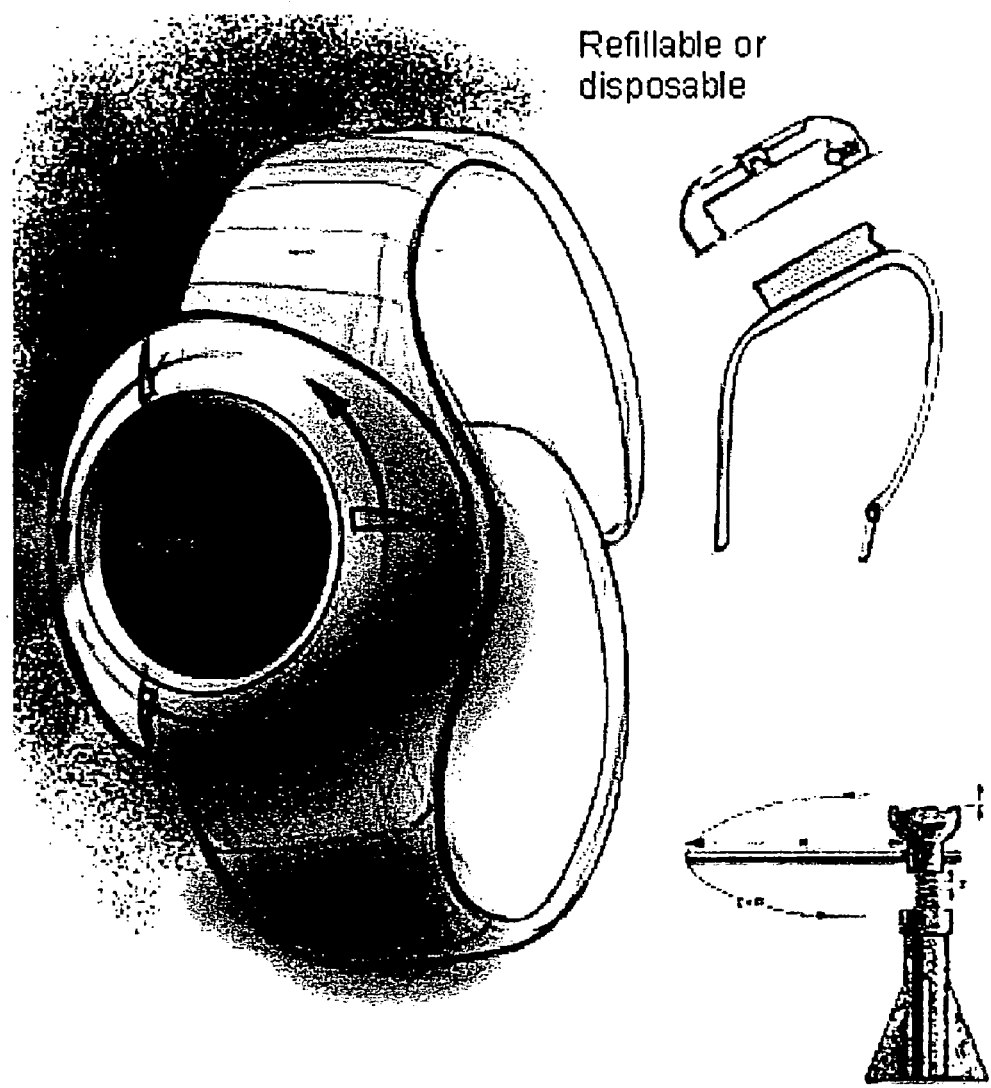
FIG. 18 is a pictorial view of a screw mechanism-based dispenser.
Figure 19:
FIG. 19 is a pictorial view of a thumbwheel-actuated dispenser.
Figure 20:
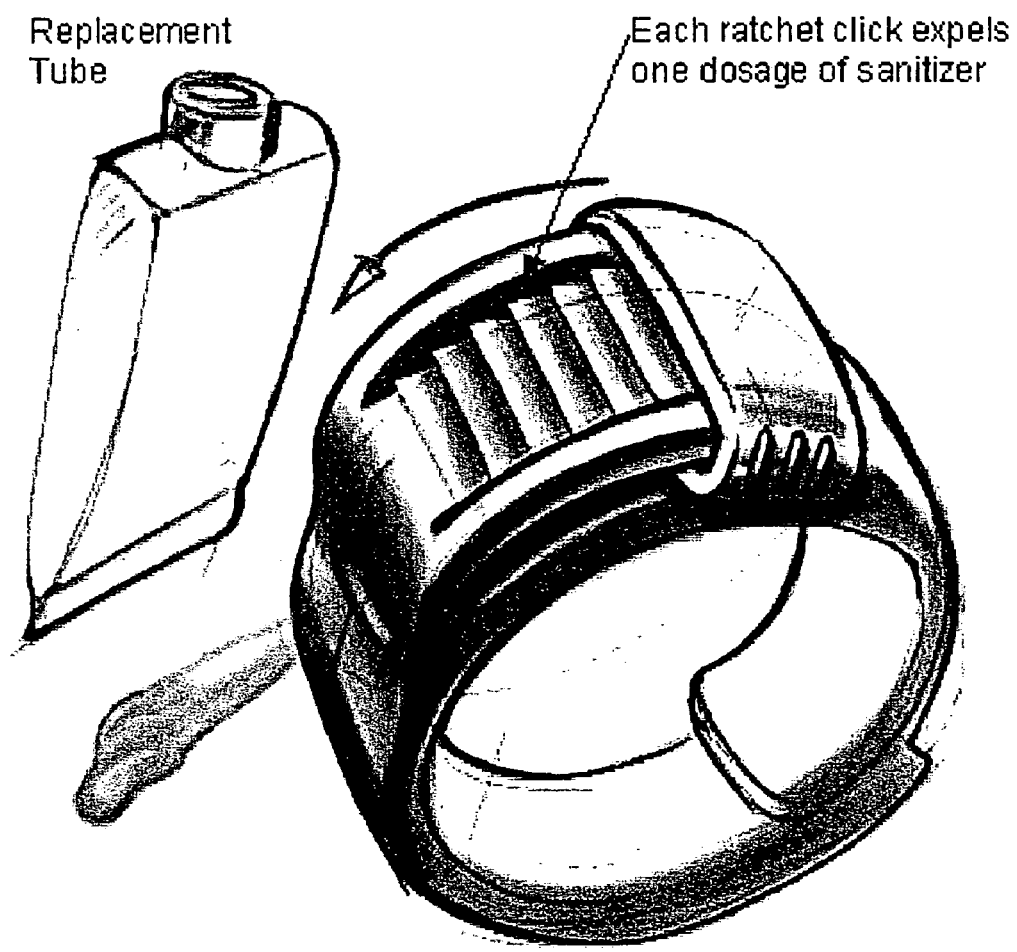
FIG. 20 is a pictorial view of a ratchet mechanism-actuated dispenser.
Figure 21:
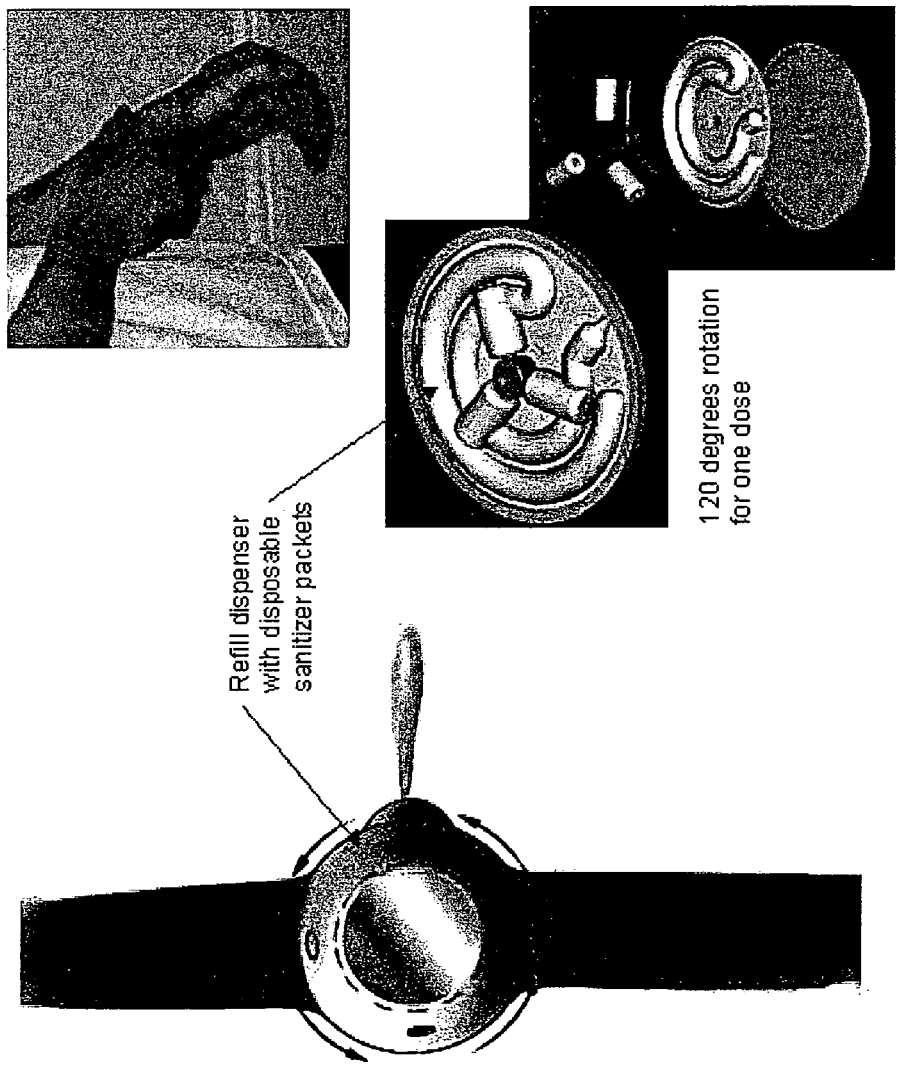
FIG. 21 is a pictorial view of a rotary compression-based dispenser.
Figure 22:
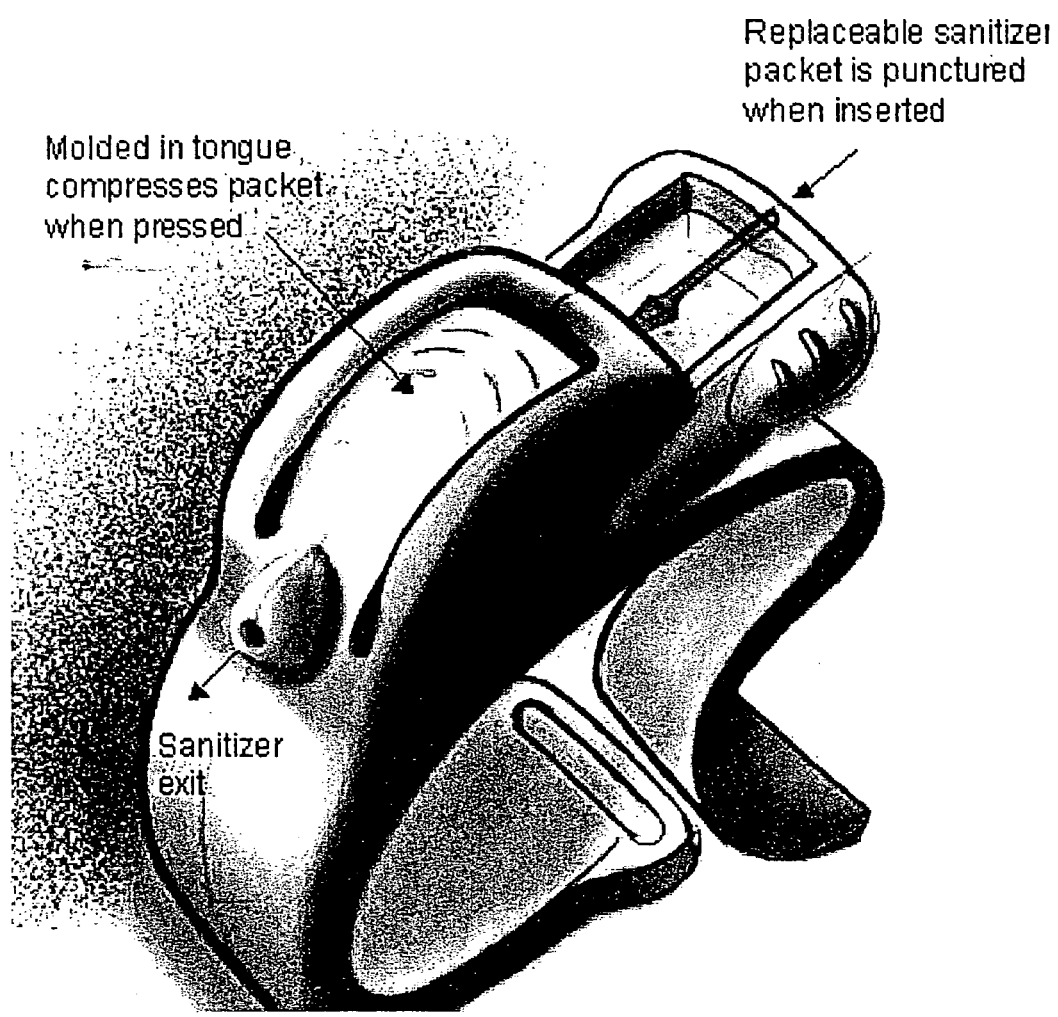
FIG. 22 is a pictorial view of a direct compression-based, packet-refillable dispenser.

FIG. 15 depicts a cartridge-based dispenser showing the disposable hand treatment-containing cartridge 311 having indentations 325 and easily punctured, self-sealing dispensing port 313. The wrist-mounted holder 323 is shown having flexible side fingers 315 which seat in indentations 325 for retaining an installed cartridge 311. The body of the holder 317 has a base plate to which is attached wristband 321. As is well known in the prior art, the cartridge 311 can be inserted into the holder 317 so as to provide leak-free dispensing of fluid through nozzle 319 upon squeezing of a deformable portion of cartridge 311.

For children, the dispenser can be in the shape of or be embossed with the logos of sports teams, super heroes, or cartoon icons. Further, dose-delivering dispensers in the shape of cartoon characters or refillable cartridge-based dispensers are feasible. With a cartridge or refillable dispenser other functions can be added to the dispenser such as having LEDs on them that light up with use. High brightness, low current LEDs as used on cell phones are quite striking. Consideration can be given to a time delay for sequential dispensing so that children would be less inclined to waste the hand treatment material. By this, is meant that it would take a minute or two before a second dose could be dispensed. This could be achieved by establishing the time constant for repressurization of the bladder using a suitably small sized air hole.

A number of more refined embodiments of the wrist mounted dispenser of hand treatments are shown in FIGS. 16 through 26. FIG. 16 depicts a siphon pump design that would be actuated by thumb pressure against a sliding actuator. Spray is ejected from the end of the actuator as fluid is siphoned from the reservoir. Another form factor for the siphon pump is provided in the design of FIG. 17 wherein the actuator is in the form of a button that can be depressed to cause ejection of hand treatment. In the designs of both FIGS. 16 and 17, two one-way check valves are employed as is common practice in the art. The design of FIG. 18 exploits a screw thread mechanism to exert pressure on a fluid. As the outer housing comprising both piston and one-way valve is rotated to cause fluid compression, the fluid is exhausted through the valve. A screw drive mechanism similar in function to those found in stick deodorant dispensers is depicted in the design of FIG. 19. A ratchet clip mechanism is used in the design of FIG. 20 to squeeze hand treatment fluid from a tube that is captivated by a ratchet housing. In FIG. 21, a design is shown which exploits a roller pump mechanism. Each incremental turn of the dispenser dial would cause a fraction of the contained fluid to be ejected while leakage past the seal is prevented by the rollers. A simple, direct pressure mechanism is used in the design of FIG. 22 to squeeze hand treatment fluid through a one-way valve, similar to an instant glue dispenser.

Preferred Embodiments

FIG. 23 is a pictorial diagram of a dispenser using the basic principle of FIG. 16. Hence, the depicted device dispenses hand treatment fluid to the hand of the arm which does not have the dispenser attached. The ejection axis for dispensing is perpendicular to the longitudinal axis of the arm to which the device is attached and fluid is dispensed onto the fingers of the actuating hand. The cross sectional view of the device is provided in FIG. 24. With respect to FIG. 23, the dispenser body 349 is shown attached to wristband 341. It comprises a hinged lid 351 that contains a hand treatment fluid refillable volume. Depression of spring-loaded pump button 343 causes the ejection of hand treatment fluid through nozzle 345.

FIG. 25 is an exploded diagram of the components of this embodiment. The upper housing 411 provides a means of enclosing, retaining, and protecting the pump assembly and actuation components. It secures actuation button 441 to lower housing 427 via interlocking pin and slot feature and retains the dispensing nozzle 433. The actuation button 441 is the primary user interface for activation of the device. The contour shape is designed to accommodate a discreet, "no-look" actuation. The piston shaft 439 is the main mechanical link between the actuation button 441 and the pump piston 435. Piston housing 437 provides precise cylinder bore for high compression dispensing of hand treatment fluid. Mechanical means of pressurizing the pump chamber 417 via displacement of actuator button 441 is provided by piston 435. It displaces hand treatment fluid through the exit port of pump chamber 417 on the dispensing stroke and provides negative pressure to draw fresh hand treatment fluid from the reservoir contained in lower housing 427 on the intake stroke. The return force necessary to drive piston 435 through the intake stroke is provided by return spring 431. Main pump chamber 417 provides the main cylinder for pressurization during dispensing and intake strokes. It integrates the valve mating surface for the exit check valve 419 and retains piston housing 437 via a precision friction slip fit. An inlet port 413 provides a precision sealing surface between the reservoir and inlet check valve 415 which seals the inlet port 413 during the dispensing stroke and hence stops hand treatment fluid backflow into the reservoir. Exit check valve 419 provides a means of sealing the pump chamber 417 during the inlet stroke, preventing air intake through dispensing nozzle 433 to reduce or eliminate pump cavitation. This nozzle establishes a calibrated orifice through which a metered dosage of hand treatment fluid can exit the dispenser. An exit tube 421 routes hand treatment fluid to the dispensing nozzle 433 and provides a means of retaining the exit check valve 419. The lower housing 427 retains the upper housing 411 and actuation button 441. It also houses the main fill port for refillable dispensers. Enclosing and sealing the main fluid reservoir is the reservoir fill lid 423. It is easily released for refilling by an ergonomic snap feature at its leading edge. O-ring 425 provides additional sealing at the fill port by compression when fill lid 423 is snapped shut. It also provides a barrier which reduces or prevents evaporation of fresh hand treatment fluid. Band pins 429 provide attachment of the dispenser assembly to the wristband 443.

Figure 23:
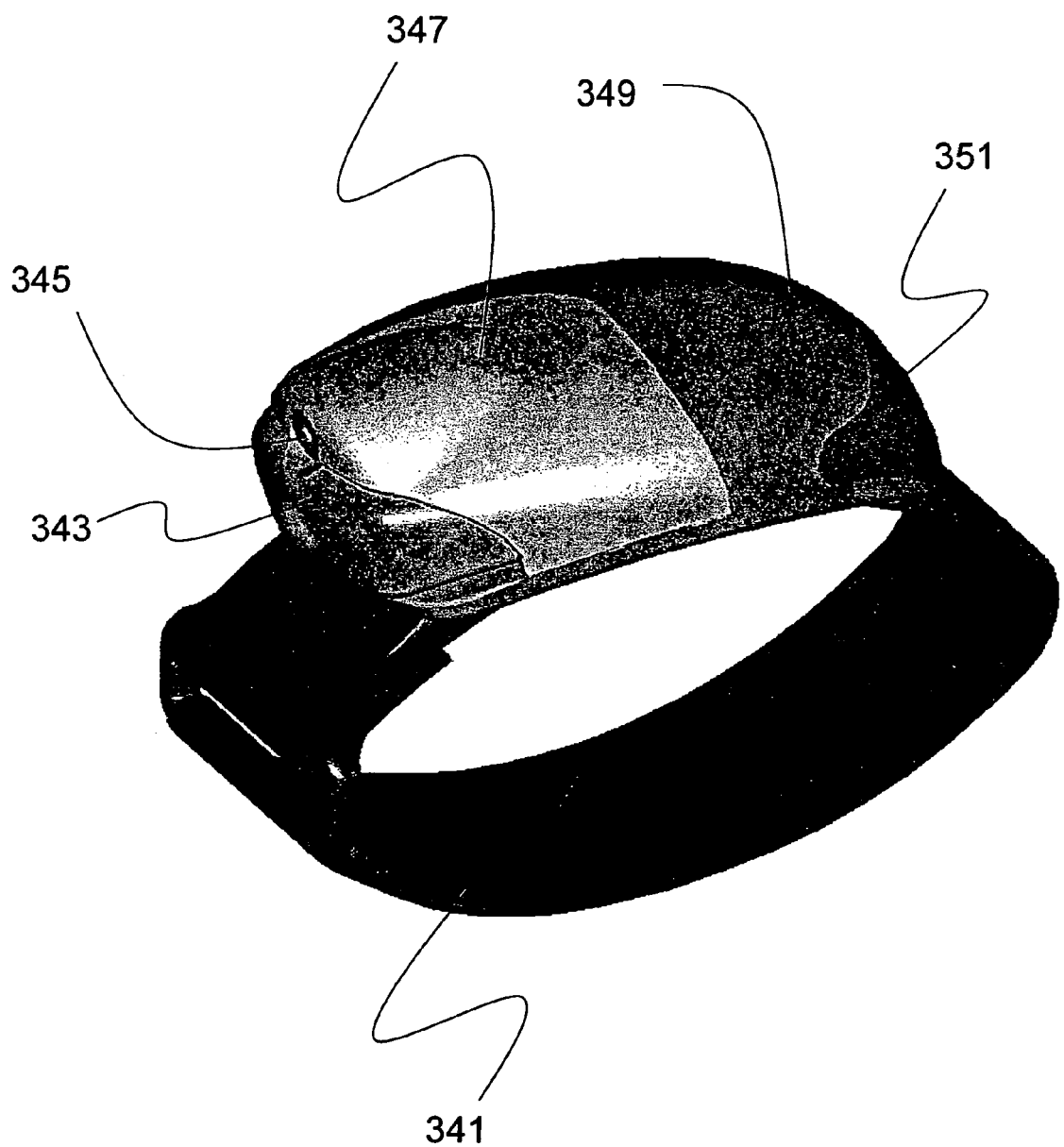
FIG. 23 is a pictorial view of refillable, of a first push button-actuated dispenser.
Figure 24:
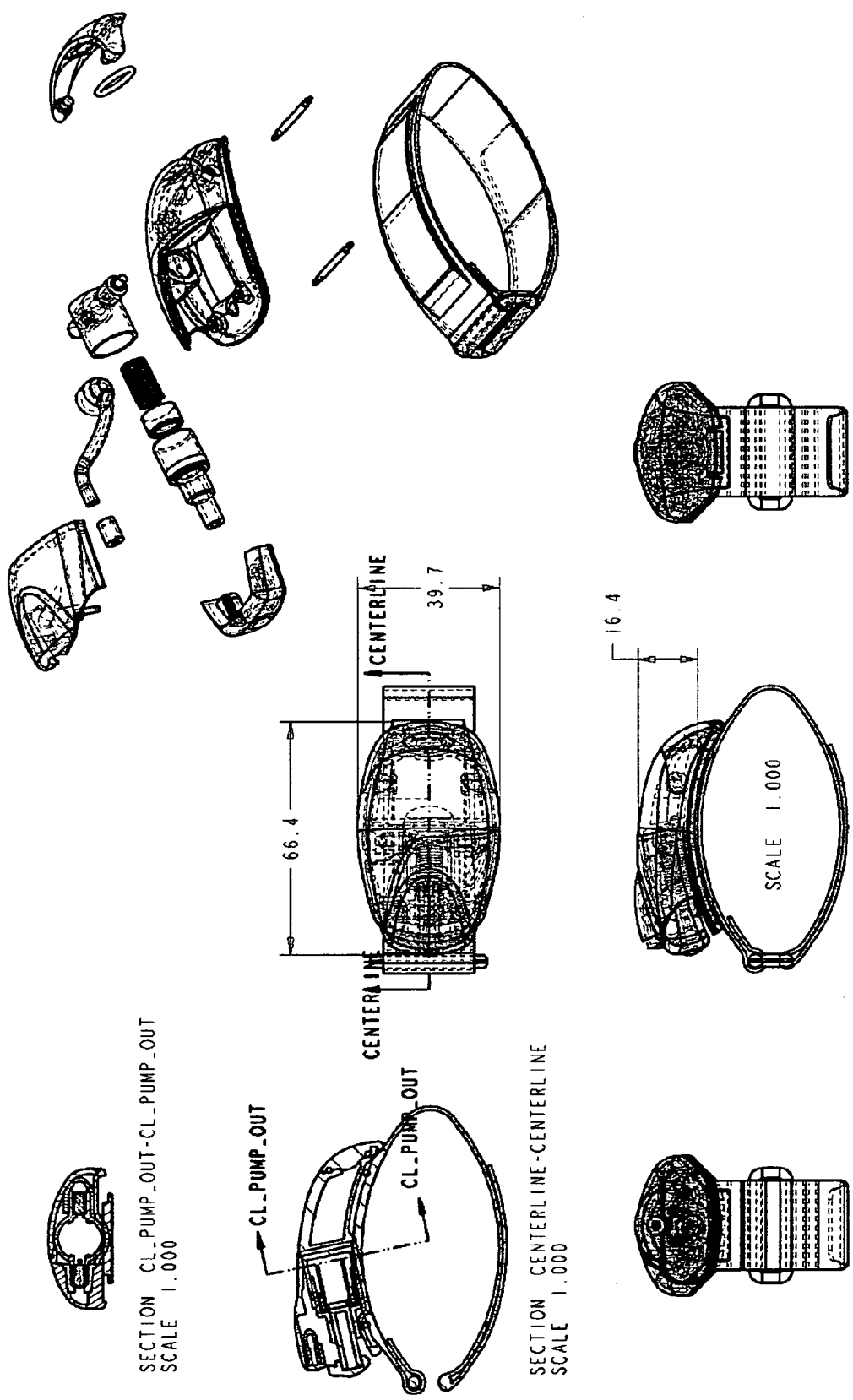
FIG. 24 is a cross-sectional view of the dispenser of FIG. 23.
Figure 25:
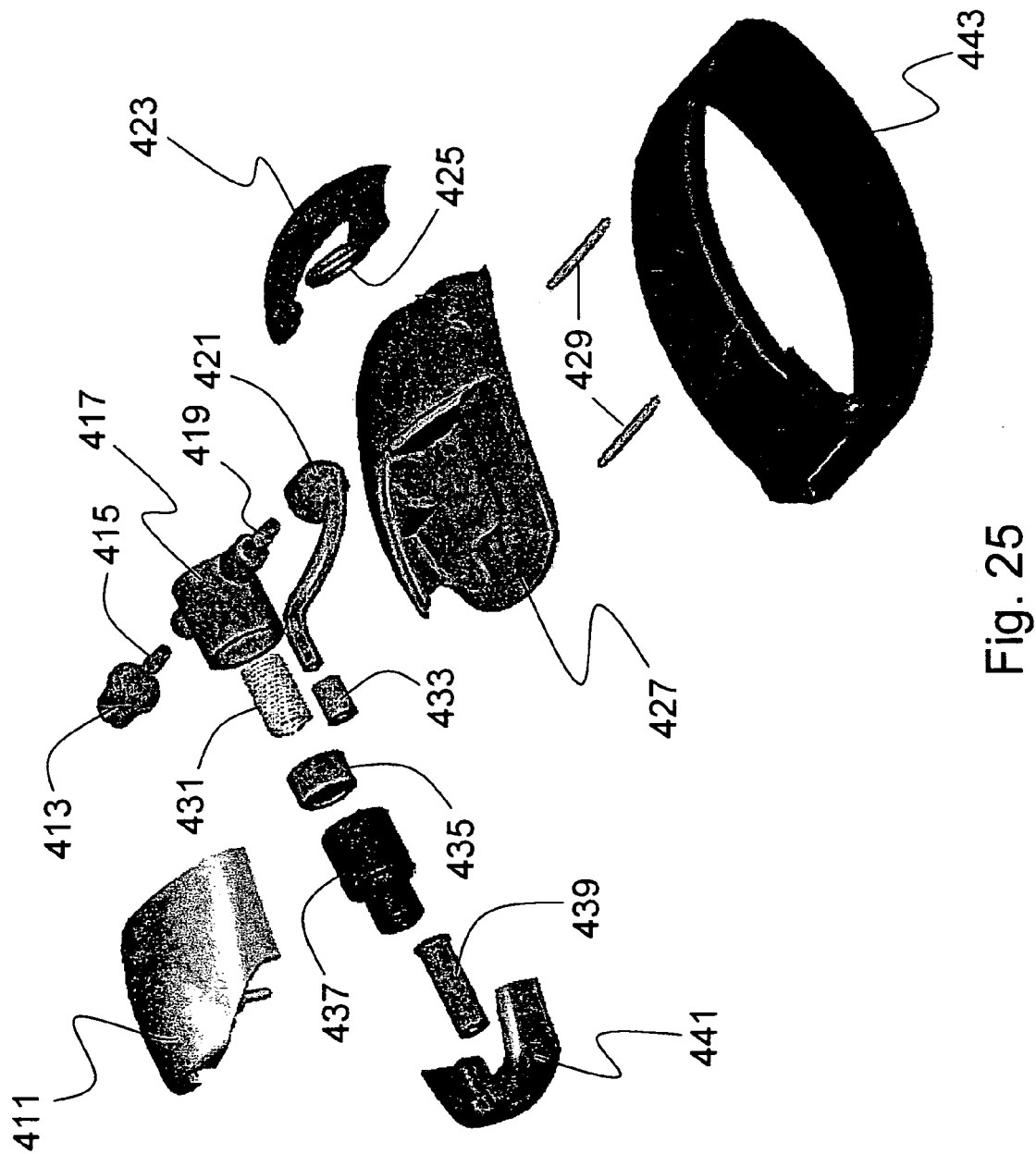
FIG. 25 is an exploded diagram of the components of the dispenser of FIG. 23.
Figure 26A:
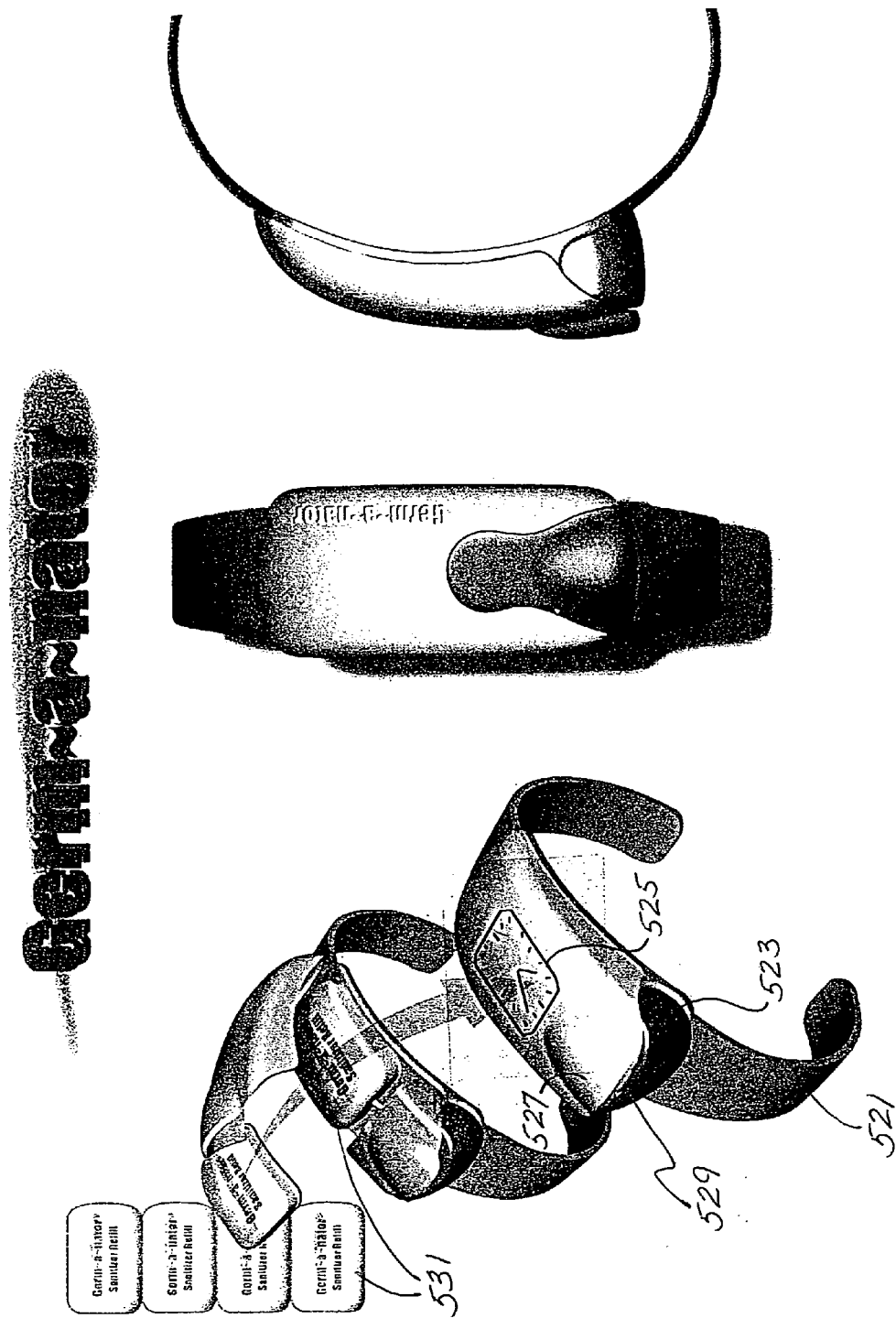
FIG. 26a is a pictorial view of refillable, second push button-actuated dispenser having a functioning watch face.

FIG. 26a is a pictorial diagram of dispenser similar to that of FIGS. 23 through 25. Shown is a functional watch face atop the dispenser top 527. The battery for this watch, not shown, can be conveniently located within the dispenser Also, in lieu of a fluid reservoir, cartridge packets 531 are used in this embodiment. The cross sectional view of the device is provided in FIG. 26b. With respect to FIG. 26b, the dispenser body is shown to be part of a wrist ring 521. It comprises a hinged top 527 that contains removable sanitizer-containing packet 531. Upon insert of packet 531 and closure of hinged top 527, the packet 531 is punctured by channel inlet 533. Retraction of spring-loaded pump button 523 creates a partial vacuum in cylinder volume 535 which is filled through channel 537 by sanitizer fluid from packet 531. Upon depression of pump button 523, backflow through channel 537 is prevented by a check valve or other means and the fluid in volume 535 is forced through channel 539 and ejected from nozzle 529.

It is to be understood that a plethora of cartridge or packet designs and form factors are within the scope of the present invention, including color-coded packets that can distinguish the type or strength of hand treatment contained therein. Also within the scope of this invention are various means to dispense hand treatment material from such packets including the mechanisms for extracting the hand treatment material from said packets. Extraction mechanisms can invoke pressure (internal or external to packet) or suction.

Figure 27:
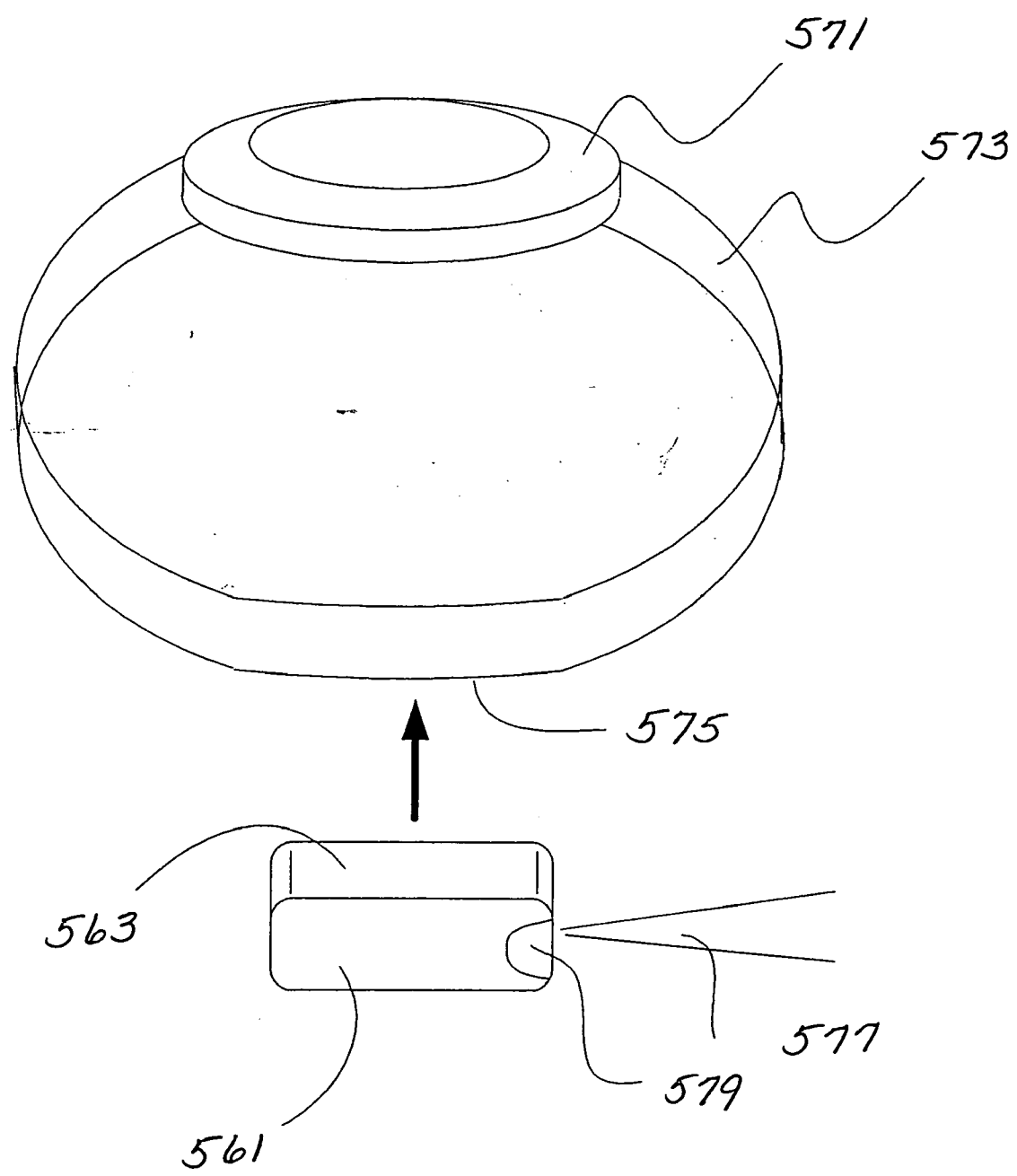
FIG. 27 is a pictorial diagram of a dispenser removably attachable to a wristwatch band.

Another category of embodiments of the present invention comprise those dispensers that are either attachable to wristwatches or are part of wristwatches or wristwatch bands. FIG. 27 depicts wristwatch 571 and band 573. A hand treatment dispenser 561 is attachable to the wristband by means of a VELCRO hook and pile material [Velcro] surface 563 that mates with a complementary VELCRO hook and pile material [Velcro] surface on the underside of the wristband 573. The dispenser 561 is shown having a push button 579 actuator that dispenses a spray 577 of hand treatment.

Pluralities of alternate attachment schemes are possible for dispensers of varying form factor. Examples of other attachment schemes include magnetic means, mechanical clips, loops, slide inserts, etc. Various types of dispensers can be made attachable including disposable, and refillable as in the case of packet dispensers described above.

Figure 28:
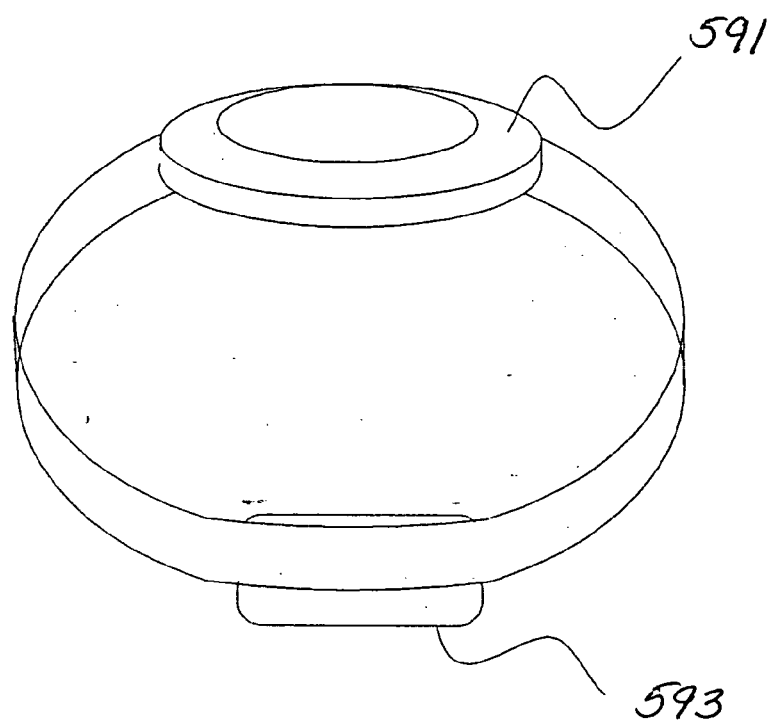
FIG. 28 is a pictorial diagram of a dispenser permanently attached to a wristwatch band.
Figure 29:
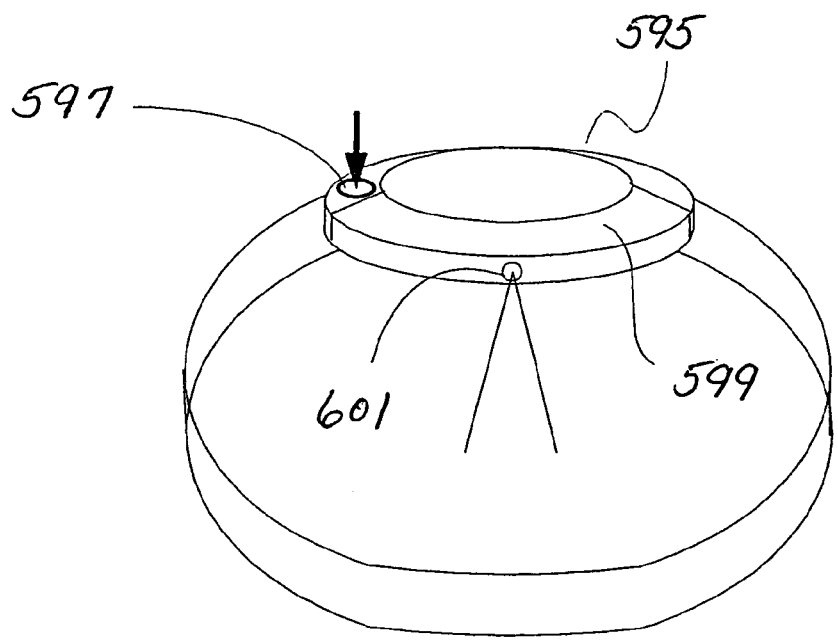
FIG. 29 is a pictorial diagram of a dispenser that is integral to the construction of a wristwatch.

FIG. 28 depicts a dispenser 593 that is manufactured as part of the wristband for watch 591 and hence would be refillable. Other schemes for fabrication of the dispenser integral to the wristband include fabricating a wristband that serves as the reservoir for hand treatment fluid and the placement of the dispenser actuator at differing positions along the wristband. FIG. 29 depicts a dispenser that is made part of the wristwatch body 595. A hinged lid 599 houses the refillable dispenser packet not shown. An actuation button 597 is depressed to cause a stream of hand treatment material to be ejected from nozzle 601.

FIG. 30 depicts a finger-mounted dispenser 631 mounted on a finger band or ring 633 and having a dispensing aperture 635. Any number of the aforementioned actuation schemes can be used in this device, so that simple compression of the exposed face of dispenser 631 will yield ejection of fluid from aperture 635.

Dispenser Types Using Other Mechanisms

Among other dispenser types are drip, pressurized, and pump-driven versions. Drip type dispensers are of limited practicality given that they are orientation sensitive. One way in which such a dispenser could be used involves actuating a shutoff valve. Various approaches well known in the prior art can be used to actuate the opening of such a valve by hand pressure. Subsequent to opening the valve, it is required to orient the dispenser to allow hand treatment to drip into the hand.

Borrowing from the technology used in the fabrication of pressurized shaving cream dispensers, there are well known methods of producing gas-pressurized streams of liquids and gels. The dispenser exploiting gas pressurization could be a low profile metal, disposable cartridge that removably attaches to a wristband.

Applicable miniature electromechanical schemes that could be used for ejecting hand treatment material are well known in the prior art. Foremost among electromechanical actuation methods is that of a solenoid. The miniature solenoids used in ink jet printing can be applied to discharging small jets of fluid. Sufficient electrical energy for hundreds of actuations can be contained in small form factor batteries such as those of the disc lithium variety. Alternatively, miniature diaphragm pumps and piezoelectric pumps used for insulin delivery can be used for discharge of small jets of fluid. Finally, in the category of thermoelectric devices, Peltier effect devices can be used with working fluids or phase change materials to effect large pressure changes with modest electrically-induced temperature changes and thereby eject fluids upon initiation of current flow into the Peltier device. In all electrical methods, a consistent fixed dosage of ejected hand treatment material can be established by electronically fixing the duration of the governing voltage or current pulse. Remote control actuation is imminently feasible with commercially-available low power consumption micro-transmitters and receivers. There are numerous ways in which such remote control can be executed, typically using the free hand or other part of the body.

A final concept is that of a dispenser similar to that of Listerine oral patches that dissolve in the mouth. Such a dispenser would dispense a sanitizing compound in the same form as the Listerine thin film, but which would disperse on the hands. Because the dispersal cannot rely on water, a particular formulation containing alcohol, perhaps using long chain hydrocarbons in concert with ethanol, would need to be used. Such an alcohol-based formulation could be a thin film formable solid until liquefied by the friction/pressure (rather than heat) of rubbing hands together.

While there have been shown and described the preferred embodiments of the present invention, it is to be understood that the invention can be embodied otherwise than is herein specifically illustrated and described and that, within such embodiments certain changes in the detail and configuration of this invention, and in the form and arrangements of the components of this invention, can be made without departing from the underlying idea or principles of this invention within the scope of the appended claims.

The invention claimed is:

1. An extremity-attachable device for storing and discharging skin treatment material, said device comprising in combination:
    a) a reservoir containing said skin treatment material;
    b) squeeze actuation means;
    c) dispensing outlet means;
    d) extremity attachment means; and
    e) flow control means further comprising
        i) air flow control means and
        ii) skin treatment flow control means,
said device capable of releasing an amount of said skin treatment material through said dispending outlet means when said actuation means is used, said air flow control means prohibiting air flow from said device during squeeze actuation for dispensing of said skin treatment material end said skin treatment control means prohibiting flow of said skin treatment material from said device when said device is not squeeze actuated, said air flow control means preventing discharge of air from volume of air within said device and said skin treatment flow control means preventing air entry into volume of skin treatment material contained within said device.

2. A device as recited in claim 1 wherein said air flow control means and said skin treatment flow control means incorporate valve means.

3. A device as recited in claim 2 wherein said device contains an internal bladder for segregating an air volume internal to said dispenser from the volume of said skin treatment material contained within said device, thereby facilitating the use of said device at arbitrary orientations with respect to gravity, independent of the relative viscosity of said skin treatment material.

4. A device as recited in claim 2 wherein said valve means further comprises check valve means.

5. A device as recited in claim 2 which includes:
    a) pump chamber;
    b) piston; and
    c) return spring,
wherein said piston is attached to said squeeze actuation means, translates within said pump chamber, upon squeeze actuation serves to displace hand treatment material through said dispensing outlet means, and provides negative pressure to draw fresh hand treatment material into said chamber upon return to its unactuated position, said return spring providing force necessary to return said piston to its unactuated position.

6. A device as recited in claim 1 wherein said reservoir comprises a deformable chamber and said squeeze actuation means comprises compressive deformation of said reservoir resulting in dispensing of said skin treatment material from said dispensing outlet means.

7. A device as recited in claim 1 in which said dispensing outlet means includes provision for adjusting the character of the dispensed material flow from streaming flow to spray.

8. A device as recited in claim 1 wherein said device is removably attached to said attachment means.

9. A device as recited in claim 1 wherein said dispensing outlet means comprises adjustable nozzle means.

10. A device as recited in claim 1 wherein said attachment means contains a working fluid volume in fluid communication with the interior of said device so that said device can be actuated by squeezing of said attachment means.

11. A device as recited in claim 1 wherein said device includes a watch.

* * * * *